(12) United States Patent
Adams et al.

(10) Patent No.: US 8,198,411 B2
(45) Date of Patent: *Jun. 12, 2012

(54) ANTI-MULLERIAN INHIBITING SUBSTANCE TYPE II RECEPTOR (MISIIR) IMMUNOCONJUGATES TO DETECT AND TREAT CANCER

(75) Inventors: Gregory P. Adams, Hatboro, PA (US); Heidi H. Simmons, Willow Grove, PA (US); Qing-an Yuan, Philadelphia, PA (US); Wayne Marasco, Wellesley, MA (US); Smita Mehta, Spartanburg, SC (US)

(73) Assignee: Fox Chase Cancer Center, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/834,338

(22) Filed: Jul. 12, 2010

(65) Prior Publication Data

US 2010/0278728 A1 Nov. 4, 2010

Related U.S. Application Data

(60) Division of application No. 11/327,917, filed on Jan. 9, 2006, now Pat. No. 7,781,568, which is a continuation-in-part of application No. PCT/US2004/022068, filed on Jul. 8, 2004.

(60) Provisional application No. 60/485,622, filed on Jul. 8, 2003.

(51) Int. Cl.
*C07K 16/18* (2006.01)
*G01N 33/53* (2006.01)

(52) U.S. Cl. .............. 530/387.1; 530/350; 530/387.3; 530/388.22; 530/387.9; 530/389.1; 530/391.3; 530/391.7; 435/7.1

(58) Field of Classification Search .................. 530/350, 530/387.1, 387.3, 387.7, 388.22, 387.9, 389.1, 530/391.3, 391.7; 435/7.1
See application file for complete search history.

(56) References Cited

FOREIGN PATENT DOCUMENTS

| WO | 95/16709 | 6/1995 |
| WO | 03/025130 | 3/2003 |

OTHER PUBLICATIONS

Terskikh, A.V., et al. ""Peptabody": a new type of high avidity binding protein." Proc Natl Acad Sci U S A. Mar. 4, 1997;94(5):1663-8.
Nord, K., et al. "Binding proteins selected from combinatorial libraries of an alpha-helical bacterial receptor domain." Nat Biotechnol. Aug. 1997;15(8):772-7.
Yuan, Q.A., et al. "Isolation of anti-MISIIR scFv molecules from a phage display library by cell sorter biopanning." Cancer Immunol Immunother. Mar. 2008;57(3):367-78. Epub Aug. 4, 2007.
Di Clemente, N., et al. "Cloning, expression, and alternative splicing of the receptor for anti-Müllerian hormone." Mol Endocrinol. Aug. 1994;8(8):1006-20.
Lee, M.M., et al. "Müllerian-inhibiting substance type II receptor expression and function in purified rat Leydig cells." Endocrinology. Jun. 1999;140(6):2819-27.
Imbeaud, S., et al. "Insensitivity to anti-müllerian hormone due to a mutation in the human anti-müllerian hormone receptor." Nat Genet. Dec. 1995;11(4):382-8.
Holmes, E.H. "PSMA specific antibodies and their diagnostic and therapeutic use." Expert Opin Investig Drugs. Mar. 2001;10(3):511-9.
Masiakos, P.T., et al. "Human ovarian cancer, cell lines, and primary ascites cells express the human Mullerian inhibiting substance (MIS) type II receptor, bind, and are responsive to MIS." Clin Cancer Res. Nov. 1999;5(11):3488-99.
McCall, A.M., et al. "Isolation and characterization of an anti-CD16 single-chain Fv fragment and construction of an anti-HER2/neu/anti-CD16 bispecific scFv that triggers CD16-dependent tumor cytolysis." Mol Immunol. May 1999;36(7):433-45.
Nielsen, U.B., et al. "Targeting of bivalent anti-ErbB2 diabody antibody fragments to tumor cells is independent of the intrinsic antibody affinity." Cancer Res. Nov. 15, 2000;60(22):6434-40.
Poul, M.A., et al. "Selection of tumor-specific internalizing human antibodies from phage libraries." J Mol Biol. Sep. 1, 2000;301(5):1149-61.
Segev, D.L., et al. "Mullerian-inhibiting substance regulates NF-kappa B signaling in the prostate in vitro and in vivo." Proc Natl Acad Sci U S A. Jan. 8, 2002;99(1):239-44. Epub Jan. 2, 2002.
Salhi, I., et al. "The anti-Müllerian hormone type II receptor: insights into the binding domains recognized by a monoclonal antibody and the natural ligand." Biochem J. May 1, 2004;379(Pt 3):785-93.

*Primary Examiner* — Stephen Rawlings
(74) *Attorney, Agent, or Firm* — Dann, Dorfman, Herrell & Skillman; Robert C. Netter, Jr.

(57) ABSTRACT

Compositions and methods for detecting and treating cancers expressing Mullerian inhibiting substance Type II receptor (MISIIR) are provided.

10 Claims, 25 Drawing Sheets

```
   1 GGCGCGCCCA CCATCACCAT CACCATCCCC CAAACAGGCG
  41 AACCTGTGTG TTCTTTGAGG CCCCTGGAGT GCGGGGAAGC
  81 ACAAAGACAC TGGGAGAGCT GCTAGATACA GGCACAGAGC
 121 TCCCCAGAGC TATCCGCTGC CTCTACAGCC GCTGCTGCTT
 161 TGGGATCTGG AACCTGACCC AAGACCGGGC ACAGGTGGAA
 201 ATGCAAGGAT GCCGAGACAG TGATGAGCCA GGCTGTGAGT
 241 CCCTCCACTG TGACCCAAGT CCCCGAGCCC ACCCCAGCCC
 281 TGGCTCCACT CTCTTCACCT GCTCCTGTGG CACTGACTTC
 321 TGCAATGCCA ATTACAGCCA TCTGCCTCCT CCAGGGAGCC
 361 CTGGACTCC TGGCTCCCAG GGTCCCCAGG CTGCCCCAGG
 401 TGAGTCCGGT ACCGTTGAGC CCAAATCTTG TGACAAAACT
 441 CACACATGCC CACCGTGCCC AGCACCTGAA CTCCTGGGGG
 481 GACCGTCAGT CTTCCTCTTC CCCCAAAAC CCAAGGACAC
 521 CCTCATGATC TCCCGGACCC CTGAGGTCAC ATGCGTGGTG
 561 GTGGACGTGA GCCACGAAGA CCCTGAGGTC AAGTTCAACT
 601 GGTACGTGGA CGGCGTGGAG GTGCATAATG CCAAGACAAA
 641 GCCGCGGGAG GAGCAGTACA ACAGCACGTA CCGTGTGGTC
 681 AGCGTCCTCA CCGTCCTGCA CCAGGACTGG CTGAATGGCA
 721 AGGAGTACAA GTGCAAGGTC TCCAACAAAG CCCTCCCAGC
 761 CCCCATCGAG AAAACCATCT CCAAAGCCAA AGGGCAGCCC
 801 CGAGAACCAC AGGTGTACAC CCTGCCCCCA TCCCGGGATG
 841 AGCTGACCAA GAACCAGGTC AGCCTGACCT GCCTGGTCAA
 881 AGGCTTCTAT CCCAGCGACA TCGCCGTGGA GTGGGAGAGC
 921 AATGGGCAGC CGGAGAACAA CTACAAGACC ACGCCTCCCG
 961 TGCTGGACTC CGACGGCTCC TTCTTCCTCT ACAGCAAGCT
1001 CACCGTGGAC AAGAGCAGGT GGCAGCAGGG GAACGTCTTC
1041 TCATGCTCCG TGATGCATGA GGCTCTGCAC AACCACTACA
1081 CGCAGAAGAG CCTCTCCCTG TCTCCGGGTA AACTCGAG
```

Figure 7

```
  1 ATGGCCCAGG TCACCTTGAA GGAGTCTGGT CCTACGCTGG
 41 TGAAACCCAC ACAGACCCTC ACGCTGACCT GCACGTTCTC
 81 TGGGTTCTCA CTCACCACTA GTGGAGTGGG TGTGGGCTGG
121 ATCCGTCAGG CCCCAGGAAA GGCCCCGGAG TGGCTTGCAC
161 TCATTGATTG GGATGACGAT AAATACTACA GCACATCTCT
201 GAAGACCAGG CTCACCATCT CCAAGGACAC CTCCAAAAAC
241 CAGGTGGTCC TTACAATGAC CAACATGGAC CCTGTGGACA
281 CAGCCACATA TTACTGTGCC CGGGACTCTT ATTATGGCTC
321 GGGGAGTCAT TTTGACTTCT GGGGCCAGGG AACCCTGGTC
361 ACCGTCTCCT CAGGTGGCGG CGGTTCCGGA GGTGGTGGTT
401 CTGGCGGTGG TGGCAGCTCC TATGAGCTGA CTCAGCCACC
441 CTCAGTGTCC GTGTCCCCTG ACAGACAGC CACCATCACC
481 TGTTCTGGAC ATGACTTGCG GAATAAATAT GCTCATTGGT
521 ATCAGCAGAA GCCAGGACAG TCCCCTGTGC TGGTCGTCTA
561 TCAAGATGCT AAGCGGCCCT CAGGAATCCC TGAGCGATTC
601 TCTGGCTCCA ACTCTGGGAA CACAGCCACT CTGACCATCA
641 GCGGGACCCA GGCTATGGAT GAGGCTGACT ATTACTGTCA
681 GACGTGGGAC AGGAGCACAG TGGTCTTCGG CGGAGGGACC
721 AAGCTGACCG TCCTAGGTCA GCCCAAGGCT GCCCCCTCGG
761 CGGCCGC
```

Figure 8A

```
MAQVTLKESGPTLVKPTQTL    20
TLTCTFSGFSLTTSGVGVGW    40
IRQAPGKAPEWLALIDWDDD    60
KYYSTSLKTRLTISKDTSKN    80
QVVLTMTNMDPVDTATYYCA   100
RDSYYGSGSHFDFWGQGTLV   120
TVSSGGGGSGGGGSGGGGSS   140
YELTQPPSVSVSPGQTATIT   160
CSGHDLRNKYAHWYQQKPGQ   180
SPVLVVYQDAKRPSGIPERF   200
SGSNSGNTATLTISGTQAMD   220
EADYYCQTWDRSTVVFGGGT   240
KLTVLGQPKAAPSAA        255
```

Figure 8B

```
  1 ATGGCCCAGG TGCAGCTGGT GCAGTCTGGA ACTGAGGTGA
 41 AGAGGCCTGG GGCCTCAGTG AAGATCTCCT GCAGGGCTAC
 81 TGGTTACACC TTTAGTGATT ATGGTATCAG TTGGATGCGA
121 CAGGCCCCTG GACAAGGGCT TGAGTGGATG GGATGGATCA
161 GCGCTTACAA TGGTAACACA AACTATGCAC AGAAGCTCCA
201 GGGCAGAGTC ACCATGACCA CAGACACGTC CACGAGCACA
241 GCCTACATGG AGCTGAGGAG CCTCAGATAT GACGACACGG
281 CCGTATATTA CTGTGCGAGA GATGGGAGGC GTGGTTCGGG
321 TATTTACTGG GGTGTGTATT ATTACAACGG TATGGACGTC
361 TGGGGCCAAG GGACCACGGT CACCGTCTCC TCAGGTGGCG
401 GCGGTTCCGG AGGTGGTGGT TCTGGCGGTG GTGGCAGTCA
441 GCCTGTGCTG ACTCAGCCAC CCTCAGCGTC TGGGACCCCC
481 GGGCAGAGGG TCACCATCTC TTGTTCTGGA AGCAGGTCCA
521 ACATCGGAAG GAATACCGTA AACTGGTATC AGCAGGTCCC
561 AGGAATGGCC CCCAAACTCC TCATCTATAG TAATAATCAG
601 CGGCCCTCAG GGGTCCTGA CCGATTCTCT GGCTCCAAGT
641 CTGGCACCTC AGCCTCCCTG GCCATCAGTG GCTCCAGTC
681 TGAGGATGAG GCTGATTATT ACTGTGCAGC ATGGGATGAC
721 AGTCTGAATG GTGTGGTATT CGGCGGAGGG ACCAAGCTGA
761 CCGTCCTAGG TCAGCCCAAG GCCGCCCCCT CGGCGGCCGC
```

Figure 9A

```
MAQVQLVQSGTEVKRPGASV     20
KISCRATGYTFSDYGISWMR     40
QAPGQGLEWMGWISAYNGNT     60
NYAQKLQGRVTMTTDTSTST     80
AYMELRSLRYDDTAVYYCAR    100
DGRRGSGIYWGVYYYNGMDV    120
WGQGTTVTVSSGGGGSGGGG    140
SGGGGSQPVLTQPPSASGTP    160
GQRVTISCSGSRSNIGRNTV    180
NWYQQVPGMAPKLLIYSNNQ    200
RPSGVPDRFSGSKSGTSASL    220
AISGLQSEDEADYYCAAWDD    240
SLNGVVFGGGTKLTVLGQPK    260
AAPSAA                  266
```

Figure 9B

```
  1 ATGGCCCAGG TGCAGCTGGT GCAGTCTGGA GGAGGCTTGG
 41 TCCAGCCTGG GGGGTCCCTG AGACTCTCCT GTGCAGCCTC
 81 TGGGTTCACC GTCAGTAGCA ACTACATGAG CTGGGTCCGC
121 CAGGCTCCAG GGAAGGGGCT GGAGTGGGTC TCAGCTATTA
161 GTGGTAGTGG TGGTAGCACA TACTACGCAG ACTCCGTGAA
201 GGGCCGGTTC ACCATCTCCA GAGACAATTC CAAGAACACG
241 CTGTATCTGC AAATGAACAG CCTGAGAGCC GAGGACACGG
281 CCGTATATTA CTGTGCGACG CGCCCTTCAA GGGGTAGCAG
321 TGGCTGGTAC GGGGGGGACT ACTGGGGCCA GGGAACCCTG
361 GTCACCGTCT CCTCAGGTGG CGGCGGTTCC GGAGGTGGTG
401 GTTCTGGCGG TGGTGGCAGC TCCTATGAGC TGACTCAGCC
441 ACCCTCAACT TCTGGGACTC CCGGGCAGAG GGTCACCATC
481 TCTTGTTCTG GAAGCACCTC CAACATCGCA ACTAATAATG
521 TAAACTGGTA CCAGTTCCTC CCAGGAACGG CCCCCAAACT
561 CCTCATGTAT CGGAATGATC AGCGGCCCGC AGGGGTCCCT
601 GACCGATTCT CTGGCTCCAA GTCTGGCACC TCAGCCTCCC
641 TGGCCATCAG TGGGCTCCAA CCTGAGGATG AGGCTGACTA
681 TTACTGTGCA GCATGGGATG ACAGCCTGGG TGGCGAGGTC
721 TTCGGAACTG GGACCAAGGT CAACGTCCTA GGTCAGCCCA
761 AGGCCGCCCC CTCGGCGGCC GC
```

Figure 10A

```
MAQVQLVQSGGGLVQPGGSL   20
RLSCAASGFTVSSNYMSWVR   40
QAPGKGLEWVSAISGSGGST   60
YYADSVKGRFTISRDNSKNT   80
LYLQMNSLRAEDTAVYYCAT  100
RPSRGSSGWYGGDYWGQGTL  120
VTVSSGGGGSGGGGSGGGGS  140
SYELTQPPSTSGTPGQRVTI  160
SCSGSTSNIATNNVNWYQFL  180
PGTAPKLLMYRNDQRPAGVP  200
DRFSGSKSGTSASLAISGLQ  220
PEDEADYYCAAWDDSLGGEV  240
FGTGTKVNVLGQPKAAPSAA  260
```

Figure 10B

```
  1 ATGGCCCAGG TGCAGCTGGT GCAGTCTGGA ACTGAGGTGA
 41 AGAGGCCTGG GGCCTCAGTG AAGATCTCCT GCAGGGCTAC
 81 TGGTTACACC TTTAGTGATT ATGGTATCAG TTGGATGCGA
121 CAGGCCCCTG GACAAGGGCT TGAGTGGATG GGATGGATCA
161 GCGCTTACAA TGGTAACACA AACTATGCAC AGAAGCTCCA
201 GGGCAGAGTC ACCATGACCA CAGACACGTC CACGAGCACA
241 GCCTACATGG AGCTGAGGAG CCTCAGATAT GACGACACGG
281 CCGTATATTA CTGTGCGAGA GATGGGAGGC GTGGTTCGGG
321 TATTTACTGG GGTGTGTATT ATTACAACGG TATGGACGTC
361 TGGGGCCAAG GGACCACGGT CACCGTCTCC TCAGGTGGCG
401 GCGGTTCCGG AGGTGGTGGT TCTGGCGGTG GTGGCAGTCA
441 GCCTGTGCTG ACTCAGCCAC CCTCAGCGTC TGGGACCCCC
481 GGGCAGAGGG TCACCATCTC TTGTTCTGGA AGCAGGTCCA
521 ACATCGGAAG GAATACCGTA AACTGGTATC AGCAGGTCCC
561 AGGAATGGCC CCCAAACTCC TCATCTATAG TAATAATCAG
601 CGGCCCTCAG GGGTCCCTGA CCGATTCTCT GGCTCCAAGT
641 CTGGCACCTC AGCCTCCCTG GCCATCAGTG GCTCCAGTC
681 TGAGGATGAG GCTGATTATT ACTGTGCAGC ATGGGATGAC
721 AGTCTGAATG GTGTGGTATT CGGCGGAGGG ACCAAGCTGA
761 CCGTCCTAGG TCAGCCCAAG GCCGCCCCC
```

Figure 11A

```
MAQVQLVQSGTEVKRPGASV    20
KISCRATGYTFSDYGISWMR    40
QAPGQGLEWMGWISAYNGNT    60
NYAQKLQGRVTMTTDTSTST    80
AYMELRSLRYDDTAVYYCAR   100
DGRRGSGIYWGVYYYNGMDV   120
WGQGTTVTVSSGGGGSGGGG   140
SGGGGSQPVLTQPPSASGTP   160
GQRVTISCSGSRSNIGRNTV   180
NWYQQVPGMAPKLLIYSNNQ   200
RPSGVPDRFSGSKSGTSASL   220
AISGLQSEDEADYYCAAWDD   240
SLNGVVFGGGTKLTVLGQPK   260
AAP                    263
```

Figure 11B

```
  1 ATGGCCCAGA TCACCTTGAA GGAGTCTGGT CCTACGCTGG TGAAACCCAC
 51 ACAGACCCTC ACGCTGACCT GCACCGTCTC TGGGTTCTCA CTCAGCAATG
101 CTAGAATGGG TGTGAGCTGG ATCCGTCAGC CCCCAGGAAA GGCCCTGGAG
151 TGGCTTGCAC TCATTTATCG GGATAATGAT AAGCGCTACA ACCCATCTCT
201 GAAGAGCAGG CTCACCATCA CCAAGGACAC CTCGAAAAAC CAAGTGGTCC
251 TGACAATGAG CAACATGGAC CCTGTGGACA CAGCCACATA TTACTGTGCA
301 CACAGCCTCG TAGTACCAGC TGCTAATCCC TTTGACTACT GGGGCCAGGG
351 AACCCTGGTC ACCGTCTCCT CATCGGCCTC GGGGGCCGAA TTGGGCGGCG
401 GCGGCTCCGG AGGAGGAGGA TCTGGTGGTG GTGGTTCGAC TAGTCAGGCT
451 GTGCTGACTC AGCCGTCTTC CCTCTCTGCA TCTCCTGGAG CATCAGCCAG
501 TCTCACCTGC ACCTTGCGCA GTGGCATCAA TGTTGGTACC TACAGGATAT
551 ACTGGTACCA GCAGAAGCCA GGGAGTCCTC CCAGTATCT CCTGAGGTAC
601 AAATCAGACT CAGATAAGCA GAAGGGCTCT GGAGTCCCCA GCCGCTTCTC
651 TGGATCCAAA GATGCTTCGG CCAATGCAGG GATTTTACTC ATCTCTGGGC
701 TCCAGTCTGA GGATGAGGCT GACTATTATT GTATGATTTG GCACACCAGC
751 GCTTATGTCT TCGGAACTGG GACCAAGGTC ACCGTCCTAG GCTCGAGC
```

Figure 14A

```
MAQITLKESGPTLVKPTQTL    20
TLTCTVSGFSLSNARMGVSW    40
IRQPPGKALEWLALIYRDND    60
KRYNPSLKSRLTITKDTSKN    80
QVVLTMSNMDPVDTATYYCA   100
HSLVVPAANPFDYWGQGTLV   120
TVSSSASGAELGGGGSGGGG   140
SGGGGSTSQAVLTQPSSLSA   160
SPGASASLTCTLRSGINVGT   180
YRIYWYQQKPGSPPQYLLRY   200
KSDSDKQKGSGVPSRFSGSK   220
DASANAGILLISGLQSEDEA   240
DYYCMIWHTSAYVFGTGTKV   260
TVLGSS                 266
```

Figure 14B

```
  1 ATGGCCGAGG TGCANCTGGT GCAGTCTGGG GGAGGCGTGG TCCAGCCTGG
 51 GAGGTCCCTG AGACTCTCCT GTGACGCCTC TGGATTCGTC TTCAGTAATT
101 ATGCTGTCCA CTGGGTCCGC CAGGCTCCAG GCAAGGGGCT AGAATGGGTG
151 GCAGCTATTT CACCTGATGG GAGGTATATA CATTATGGAG ACTCCGTGCA
201 GGGCCGATTC ACCGTGTCCA GAGACAACGC CCAGAGCACC CTGTATCTGC
251 AAATGAACAG TCTGAGAGCC GAGGACACGG CTGTCTATTA TTGTGCAAGA
301 GATCGAGGGA GGCCTGATGC TTTCGATATC TGGGGCCAAG GGACAATGGT
351 CACCGTCTCT TCAGGTGGCG GCGGTTCCGG AGGTGGTGGT TCTGGCGGTG
401 GTGGCAGCCA GTCTGTGCTG ACTCAGCCAC CCTCCGCGTC CGGGTCTCCT
451 GGACAGTCAG TCACCATCTC CTGCACCGGA ACCAGCAGTG ACGTTGGCGC
501 TTATGACCAT GTCTCTTGGT ACCAACAACA CCCAGACAAA GCCCCCAAAC
551 TCATCATTTA TGAGGTCAAT AGACGGCCCT CAGGGGTCCC TGATCGCTTC
601 TCTGGCTCCA AGTCTGGCAA CACGGCCTCC CTGACCGTCT CTGGCCTCCA
651 GATTGAGGAT GAGGCTGATT ACTTCTGCAC CTCATATTCA CGAATTAACG
701 ATTATGTCTT CGGACCTGGG ACCAGGGTCG CCGTCCTCGG TCAGCCCAAG
751 GCTACCCCCT CGGCGGCCGC A
```

Figure 15A

```
MAEVXLVQSGGGVVQPGRSL    20
RLSCDASGFVFSNYAVHWVR    40
QAPGKGLEWVAAISPDGRYI    60
HYGDSVQGRFTVSRDNAQST    80
LYLQMNSLRAEDTAVYYCAR   100
DRGRPDAFDIWGQGTMVTVS   120
SGGGGSGGGGSGGGGSQSVL   140
TQPPSASGSPGQSVTISCTG   160
TSSDVGAYDHVSWYQQHPDK   180
APKLIIYEVNRRPSGVPDRF   200
SGSKSGNTASLTVSGLQIED   220
EADYFCTSYSRINDYVFGPG   240
TRVAVLGQPKATPSAAA      257
```

Figure 15B

```
  1 ATGGCTCAGG TGCAGCTGGT GCAGTCTGGG GCTGAGGTGA AGAAGCCTGG
 51 GGCCTCAGTG AAGGTCTCCT GCAAGGCTTC TGGATACACC TTCACCAGTT
101 ATGATATCAA CTGGGTGCGA CAGGCCACTG GACAAGGGCT TGAGTGGATG
151 GGATGGATGA ACCCTAACAG TGGTAACACA GGCTATGCAC AGAAGTTCCA
201 GGGCAGAGTC ACCATGACCA GGAACACCTC CACTAATACA GCCTACATGG
251 AACTGACCAG CCTGACATCT GAGGACACGG CCGTGTATTA CTGTGCGAGA
301 GGCAGCCCAT CCCCGATGAA CGTCTGGGGC AAGGGACCA CGGTCACCGT
351 CTCCTCAGGT GGCGGCGGTT CCGGAGGTGG TGGTTCTGGC GGTGGTGGCA
401 GCCAGCCTGT GCTGACTCAG CCCCACTCTG TGTCGGAGTC TCCGGGGAAG
451 ACGGTAACCA TCTCCTGCAC CCGCAGCAGT GGGAGCATTG CCAACGACTA
501 TGTTCAGTGG TTCCAGCAGC GCCCGGGCAG TGCCCCCACC ATTGTGATCT
551 ATGAAGATTA CCGAAGACCC TCTGGGGTCC CTGATCGGTT CTCTGGCTCC
601 ATCGACAGCT CCTCCAACTC TGCCTCCCTC ACCATCTCTG GACTGAAGAC
651 TGAGGACGAG GCTGACTACT ACTGTCAGTC TTATGATAGC AGCAATCCTT
701 ATGTGGTATT CGGCGGAGGG ACCAAGCTGA CCGTCCTAGG TCAGCCCAAG
751 GCTGCCCCCT CGGCGGCCGC A
```

Figure 16A

```
MAQVQLVQSGAEVKKPGASV    20
KVSCKASGYTFTSYDINWVR    40
QATGQGLEWMGWMNPNSGNT    60
GYAQKFQGRVTMTRNTSTNT    80
AYMELTSLTSEDTAVYYCAR   100
GSPSPMNVWGQGTTVTVSSG   120
GGGSGGGGSGGGGSQPVLTQ   140
PHSVSESPGKTVTISCTRSS   160
GSIANDYVQWFQQRPGSAPT   180
IVIYEDYRRPSGVPDRFSGS   200
IDSSSNSASLTISGLKTEDE   220
ADYYCQSYDSSNPYVVFGGG   240
TKLTVLGQPKAAPSAAA      257
```

Figure 16B

```
  1 mlgslglwal lptaveappn rrtcvffeap gvrgstktlg elldtgtelp rairclysrc
 61 cfgiwnltqd raqvemqgcr dsdepgcesl hcdpsprahp spgstlftcs cgtdfcnany
121 shlpppgspg tpgsqgpqaa pgesiwmalv llglflllll llgsiilall qrknyrvrge
181 pvpeprpdsg rdwsvelqel pelcfsqvir egghavvwag qlqgklvaik afpprsvaqf
241 qaeralyelp glqhdhivrf itasrggpgr llsgpllvle lhpkgslchy ltqytsdwgs
301 slrmalslaq glaflheerw qngqykpgia hrdlssqnvl iredgscaig dlglalvlpg
361 ltqppawtpt qpqgpaaime agtqrymape lldktldlqd wgmalrradi yslalllwei
421 lsrcpdlrpd sspppfqlay eaelgntpts delwalavqe rrrpyipstw rcfatdpdgl
481 relledcwda dpearltaec vqqrlaalah pqeshpfpes cprgcpplcp edctsipapt
541 ilpcrpqrsa chfsvqqgpc srnpqpactl spv
```

Figure 17

ANTI-MULLERIAN INHIBITING SUBSTANCE TYPE II RECEPTOR (MISIIR) IMMUNOCONJUGATES TO DETECT AND TREAT CANCER

This application is a divisional application of U.S. patent application Ser. No. 11/327,917, filed Jan. 9, 2006, now U.S. Pat. 7,781,568, which is a continuation-in-part of PCT/US2004/022068, filed Jul. 8, 2004, which claims priority to U.S. Provisional Application 60/485,622 filed Jul. 8, 2003. The entire disclosure of each of these applications is incorporated by reference herein.

Pursuant to 35 U.S.C. Section 202(c), it is acknowledged that the United States Government has certain rights in the invention described herein, which was made in part with funds from United States National Cancer Institute, Grant No. 2P50 CA83638.

FIELD OF THE INVENTION

The present invention relates to the fields of immunology and cancer treatment. Specifically, compositions and methods for detecting and treating cancers expressing Mullerian inhibiting substance Type II receptor (MISIIR) are disclosed.

BACKGROUND OF THE INVENTION

Several publications and patent documents are cited throughout the specification in order to describe the state of the art to which this invention pertains. Each of these citations is incorporated herein by reference as though set forth in full.

The precise targeting specificity of antibody molecules makes them attractive vehicles for tumor imaging and therapy agents. Employing an antibody with a high affinity for an antigen that is uniquely or predominantly expressed on cancer cells can lead to a greater specificity of tumor retention, thereby increasing the likelihood of successful treatment or detection. While the initial clinical trials of antibody-based tumor targeting revealed a number of hurdles (e.g., the immunogenicity of the murine monoclonal antibodies, the poor tumor penetration of immunoconjugates and a lack of tumor specificity of the antigenic targets), these have largely been addressed over the past decade. Anti-tumor antibodies are now developed using human immunoglobulin genes, resulting in proteins that are rarely seen as foreign. The degree of tumor penetration and the rate of systemic elimination of toxic immunoconjugates have been improved through the development of novel, minimal antibody-based structures (e.g., monovalent and divalent single-chain Fv [scFv] molecules). In preclinical models, this has simultaneously increased the fraction of the tumor that is treated and reduced the exposure of normal tissues (e.g., bone marrow) to the immunoconjugate (Adams, G. P. (1998) In Vivo, 12:11-22). Additionally, a second generation of tumor-associated or tumor-specific antigenic targets combines a predominantly tumor-specific expression pattern with an antibody-triggered alteration in intracellular signaling. The targeting of cytotoxic agents, such as radioisotopes or drugs, to such an antigen can lead to an additive or synergistic anti-tumor effect.

Monoclonal antibody (MAb)-based immunotherapy has shown notable promise in the treatment of hematologic malignancies (Kaminski, M. S., et al. (1993) N. Engl. J. Med., 329:459-465; Press, O. W., et al. (1993) N. Engl. J. Med., 329:1219-1224). Despite some constraints imposed by tumor physiology (Jain, R. K., et al. (1987) 47:3039-3051), two of the four members of the HER/EGF receptor family have proven to be useful targets for antibody-based therapy of cancer. MAbs specific for HER2/neu (Harweth, I. M., et al. (1993) Br. J. Cancer, 68:1140-1145) and EGFR (Fan, Z., et al. (1993) 53:4322-4328) can inhibit the growth of human tumors that overexpress their respective target antigens in immunodeficient mice. Treatment with a humanized form of the anti-HER2/neu 4D5 MAb (HERCEPTIN™) leads to clinical responses alone and in combination with chemotherapy agents in clinical trials and is licensed for use in breast cancer (Baselga, J., et al. (1996) J. Clin. Oncol., 14:737-744; Baselga, J. (2001) J. of Cancer, 37 Suppl:S18-24). A number of clinical trials also have focused on the efficacy of antibodies that target therapeutic radioisotopes to tumors (radioimmunotherapy or RAIT). Of note, the U.S. Food and Drug Administration (F.D.A.) has approved commercial RAIT drugs ZEVALIN™, a conjugate of an anti-CD20 monoclonal antibody and the beta-emitting radioisotope Yttrium-90 [$^{90}$Y] for the treatment of non-Hodgkin's lymphoma, and BEXXAR®, iodine-131 [$^{131}$I] Tositumomab for the treatment of non-Hodgkin's lymphoma.

Radiolabeled MAbs have also been used for the radioimmunodetection (RAID) of a number of types of tumors including pancreatic cancer (Gold, D., et al. (2001) Crit. Rev. Oncol.-Hemat., 39:147-154), non small cell lung cancer (Schillaci, O., et al. (2001) Anticancer Res., 221:3571-3574), ovarian cancer (Kalofonos, H. P., et al. (1999) Acta Oncol., 38:629-634), colorectal carcinoma (Wong, J., et al. (1997) J. of Nuc. Med., 38:1951-1959; Willkomm, P., at al. (2000) J. of Nuc. Med., 41:1657-1663), and prostate cancer (Fang, D. X., et al. (2000) Tech. Urology, 6:146-150). These studies report the ability to detect lesions that are detectable by other methodologies (e.g., computerized tomography (CT) and magnetic resonance imaging; MRI). Immunodetection can be improved upon, however, by employing smaller, engineered antibody-based molecules such as scFv (Begent, R. H., et al. (1996) Nat. Med., 2:979-984). When isotopes with relatively short half-lives are to be used, molecules like the small, divalent diabody should exhibit the greatest degree of specific tumor localization in a setting of low normal organ background (Williams, L. E., et al. (2001) Cancer Biother. And Radiopharm., 16:25-35). Furthermore, RAID studies can be effectively utilized to acquire predictive dosimetry for use in planning or ensuring safety of subsequent RAIT studies.

Mullerian inhibiting substance (MIS) is a member of the transforming growth factor-β (TGFβ) superfamily of secreted protein hormones that signal through receptor complexes of type I and type II serine/threonine kinase receptors. The binding of MIS ligand to its receptor initiates a signaling cascade, including phosphorylation of Smad1, that is dependent on recruitment of type I receptors, ALK2 and ALK6, which also signal for bone morphogenetic proteins (Segev, D. L., et al. (2001) J. of Biol. Chem., 276:26799-26806). In males, MIS is produced in fetal and postnatal testes. MIS binds to its receptor and triggers regression of the Mullerian ducts, the anlagen of the uterus, fallopian tubes and vagina (Hudson, P. L., at al. (1990) J. Clin. Endocrinol. Metab., 70:16-22). In contrast, MIS is not produced in females until adolescence, thus allowing the above tissues to develop (Hudson, P. L., et al. (1990) J. Clin. Endocrinol. Metab., 70:16-22).

In adult females, MIS type II receptor (MISIIR) is expressed on the surface epithelium of the ovaries (Masiakos, P. T., et al. (1999) Clin. Cancer Res., 5:3488-3499). In mice, MISIIR mRNA has been detected in ovarian surface epithelium (MOSE cells) and ovarian tissue (Connolly, D. C., et al. (2003) Cancer Res., 1389-1397). In rats, MISIIR mRNA has been detected in embryonic, pubertal, and adult testes; the uterus; the ovaries; and the embryonic lung (Teixeira et al. (1996) Endocinology, 137:160-165; Catlin et al. (1997)

Endocrinology, 138:790-796). Additionally, MISIIR has been detected in human cervical cancer cells, prostate cancer cells, breast epithelial cells, breast cancer cell lines, breast fibroadenomas, breast tumors, and ductal carcinomas (Segev et al. (2000) J. Biol. Chem., 275:28371-28379; Segev et al. (2001) J. Biol. Chem., 276:26799-26806; Segev et al. (2002) Proc. Natl. Acad. Sci., 99:239-244; Barbie et al. (2003) Proc. Natl. Acad. Sci., 100:15601-15606).

Coelomic epithelium is the most common origin of human ovarian cancers and tumors of this origin express the MIS type II receptor. MISIIR mRNA is expressed in a number of ovarian carcinoma cell lines, including OVCAR3, OVCAR5, OVCAR8, OV1063 and SKOV3 (Masiakos, P. T. et al., (1999) Clin. Cancer Res., 5:3488-3499). Furthermore, recombinant MIS bound tumor cells isolated from ascites in 15 of 27 (56%) ovarian cancer patients and the binding of recombinant MIS to these tumor cells led to significant growth inhibition in 22/27 (82%) of these cases (Masiakos, P. T. et al., (1999) Clin. Cancer Res., 5:3488-3499). These findings demonstrate the relevance of MISIIR for anti-cancer therapies, particularly ovarian cancer.

SUMMARY OF THE INVENTION

In accordance with the present invention, novel antibody molecules having specific binding affinity for the Mullerian Inhibiting Substance II Receptor (MISIIR) are provided. Such antibodies include, monoclonal, polyclonal, diabodies, tribodies, single domain antibodies, and scFv. In a particular embodiment, the antibodies molecules are single chain Fv antibody molecules. In another embodiment of the invention, the single chain Fv antibody molecules comprise an amino acid sequence selected from the group consisting of SEQ ID NOS: 9-15.

In yet another embodiment, molecules comprising the single chain Fv antibody molecules of the invention are disclosed. Such molecules include without limitation, a diabody, a tribody, a tetrabody, an immunotoxin, a recombinantly produced IgG, Fab, Fab', F(ab')$_2$, F(v), scFv, scFv$_2$, scFv-Fc, minibody, a bispecific antibody, an AFFIBODY® domain Z of *staphylococcus* protein A molecule, and a peptabody.

In a preferred embodiment, the antibody of the invention has binding affinity for the extracellular domain of MISIIR. More preferably, the antibodies bind MIS binding sites. Such sites include, for example, the amino acid sequences of SEQ ID NOS: 16-18.

According to another aspect of the invention, compositions and methods for treating cancer are provided wherein a patient is administered a therapeutically effective amount of the anti-MISIIR molecules of the invention in a pharmaceutically acceptable carrier. In a particular embodiment of the invention, the cancer is selected from the group consisting of breast, prostate, cervical, ovarian, testicular, and pulmonary cancers. In a specific embodiment, the cancer is ovarian cancer. In accordance with another aspect of the instant invention, the anti-MISIIR antibody molecule can be conjugated to at least of the following agents, a chemotherapeutic agent, a radioisotope, a toxin, a magnetic bead, a detectable label and a pro-drug.

In yet another embodiment of the invention, the anti-MISIIR antibodies are administered to a patient in combination with, prior to, or after administration of chemotherapeutic agents.

According to yet another aspect of the invention, compositions and methods for imaging cancer, particularly ovarian cancer, are provided wherein a patient is administered a sufficient amount of an anti-MISIIR antibody molecule. In another embodiment, the anti-MISIIR antibody is labeled with a radioisotope and/or a contrast agent. The patient can be scanned by medical devices such as, without limitation, gamma cameras, mammography instruments, positron emission tomography (PET) cameras, and magnetic resonance imaging (MRI) imaging.

In another embodiment of the instant invention, anti-MISIIR antibodies are employed to detect the presence of MISIIR in patients suspected of having cancer, particularly ovarian cancer. According to one aspect, the anti-MISIIR antibodies are employed as a diagnostic tool. In another embodiment of the instant invention, the presence of MISIIR is detected in tissues and/or fluids, such as blood, from a patient to monitor progression or remission of disease.

BRIEF DESCRIPTIONS OF THE DRAWING

FIG. 1 is an image of a Western blot of the purification of an MISIIR fusion protein. Proteins were separated by SDS-polyacrylamide gel electrophoresis and detected by anti-His tag monoclonal antibodies.

FIG. 2 depicts the results of a PCR fingerprinting assay. The restriction patterns of 10 clones were analyzed on an agarose gel. Unique patterns are noted in lanes 1-7, 9, and 10. M lane is molecular weight markers.

FIG. 3 is a graph of the eluted protein from the SuperDex75 size exclusion column on an HPLC system. Samples were taken over 30 minutes at intervals of 0.1 seconds. The large peak (of which most is above the field of view) is labeled as the scFv of clone #7A.

FIG. 4 is an image of a polyacrylamide gel electrophoresis analysis of the proteins eluted from the size exclusion chromatography assay. Lanes 1-5 are the elution fractions 12-16. Lane MW contains molecular weight standards and the sizes of two of the molecular weight standards are indicated at the right of the gel.

FIG. 7 is a nucleotide sequence (SEQ ID NO: 8) encoding for the fusion of the extracellular domain of MISIIR and Fc.

FIGS. 8A and 8B are the nucleotide sequence (SEQ ID NO: 1) and amino acid sequence (SEQ ID NO: 9) of the scFv antibody molecule of clone #17.

FIGS. 9A and 9B are the nucleotide sequence (SEQ ID NO: 2) and the amino acid sequence (SEQ ID NO: 10) of the scFv antibody molecule of clone #23.

FIGS. 10A and 10B are the nucleotide sequence (SEQ ID NO: 3) and amino acid sequence (SEQ ID NO: 11) of the scFv antibody molecule of clone #29.

FIGS. 11A and 11B are the nucleotide sequence (SEQ ID NO: 4) and amino acid sequence (SEQ ID NO: 12) of the scFv antibody molecule of clone #7.

FIGS. 14A and 14B are the nucleotide sequence (SEQ ID NO: 5) and the amino acid sequence (SEQ ID NO: 13) of the GY4 scFv antibody molecule.

FIGS. 15A and 15B are the nucleotide sequence (SEQ ID NO: 6) and the amino acid sequence (SEQ ID NO: 14) of the M2 scFv antibody molecule.

FIGS. 16A and 16B are the nucleotide sequence (SEQ ID NO: 7) and the amino acid sequence (SEQ ID NO: 15) of the M9 scFv antibody molecule.

FIG. 17 provides the amino acid sequence from GENBANK® Accession No. NP_065434. The amino acid sequence is SEQ ID NO. 19.

DETAILED DESCRIPTION OF THE INVENTION

In accordance with the present invention, anti-MISIIR antibodies and methods of use thereof are provided. Specifically, methods for the immunodetection and imaging of cancer associated with MISIIR expression and methods of treating the same are provided.

The antibodies of the invention include monoclonal, polyclonal, scFv and molecules comprising a plurality of scFv. Also encompassed by the present invention are conjugates of the antibody molecules described herein. Such conjugates include, without limitation, antibodies operably linked to imaging reagents, contrast agents, chemotherapeutic agents, cytotoxic molecules (e.g., immunotoxins) and the like.

scFv molecules specific for human tumor-associated antigens have been previously shown to be retained in a highly specific manner in human tumor xenografts growing in immunodeficient mice (Schier, R., et al. (1995) Immunotechnology, 1:63-71). Notably, quantitative tumor retention can be significantly enhanced by utilizing divalent scFv with a higher avidity for the antigen (Adams, G. P., et al. (1993) Cancer Res., 53:4026-4034). Additionally, the structure of the divalent scFv can influence the degree of localization in a tumor, with non-covalent diabodies typically exhibiting four-fold greater localization at 24 hours post injection that was seen with the gene-fused or chemically conjugated scFv dimers (Adams, G. P., et al. (1998) British J. Cancer, 77:1405-1412).

Figure 6:
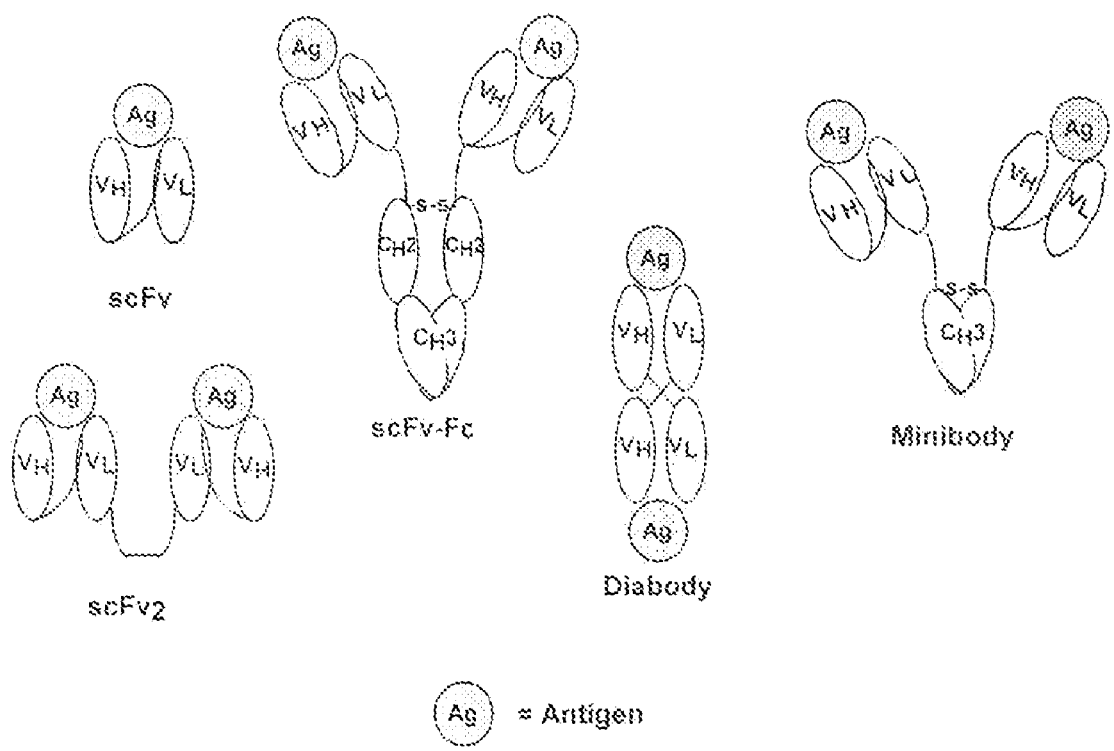
FIG. 6 is a schematic drawing of examples of the scFv-based antibodies that may be employed as anti-MISIIR antibodies.

In addition to avidity and structure, binding affinity can also influence the targeting properties of scFv molecules. Very high affinity (e.g., greater than $10^{-9}$ M) has been associated with reduced tumor localization and poor tumor penetration of scFv, likely due to a saturation of the antigen pool in the perivascular region of the tumor (Adams, G., et al. (1998) Cancer Res., 58:485-490; Adams, G. P., et al. (2001) Cancer Res., 61:4750-4755). In these studies, very high affinity ($10^{-11}$ M) anti-HER2/neu scFv molecules were observed by immunofluorescence to only penetrate a few cell lengths from blood vessels while low affinity ($10^{-7}$ M or less) scFv targeting the same antigenic epitope exhibited a diffuse penetration. Therefore, antibody molecules with very high affinity may not be the most desirable for immunotherapy with antibodies conjugated, e.g., to radioisotopes or chemotherapeutic agents as the conjugated antibodies may not penetrate efficiently enough in a short period of time. Unconjugated antibody molecules (i.e. lacking radioactive particles or chemotherapeutic agents) with very high affinity may be preferred for therapy, however, as they have significantly longer time to penetrate into the tumor to kill target cells. FIG. 6 shows some of the constructs that can be generated and used as anti-MISIIR antibodies. As noted herein, some of the divalent structures may exhibit improved retention or greater internalization, depending upon the affinity and the target epitope.

In a particular embodiment, the anti-MISIIR antibodies of the instant invention are directed to specific regions of MISIIR (see, e.g., GENBANK® Accession Nos. NP_065434 and NM_020547). Specifically, the anti-MISIIR antibodies are directed to regions of MISIIR which interact with MIS. These regions include, without limitation, amino acids 46-59 (GTELPRAIRCLYSR; SEQ ID NO: 16), amino acids 92-109 (CDPSPRAHPSPGSTLFTC; SEQ ID NO: 17), and amino acids 81-101 (DSDEPGCESLH-CDPSPRAHPS; SEQ ID NO: 18).

Exemplary amino acid sequences of anti-MISIIR antibodies of the instant invention include SEQ ID NOS: 9-15. See FIGS. 8B-11B and FIGS. 14B-16B. Nucleic acid molecules encoding these antibodies are also encompassed by the present invention. For example, SEQ ID NOS: 1-7.

I. Definitions

The following definitions are provided to facilitate an understanding of the present invention:

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" may refer to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., (1989) Molecular Cloning, Cold Spring Harbor Laboratory):

$$Tm=81.5° C.+16.6 \text{ Log } [Na+]+0.41(\% \; G+C)-0.63(\% \text{ formamide})-600/\#bp \text{ in duplex}$$

As an illustration of the above formula, using [Na+]=[0.368] and 50% formamide, with GC content of 42% and an average probe size of 200 bases, the Tm is 57° C. The Tm of a DNA duplex decreases by 1-1.5° C. with every 1% decrease in homology. Thus, targets with greater than about 75% sequence identity would be observed using a hybridization temperature of 42° C. For example, hybridizations may be performed, according to the method of Sambrook et al., (supra) using a hybridization solution comprising: 5×SSC, 5×Denhardt's reagent, 1.0% SDS, 100 μg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37.0 in 1×SSC and 1% SDS; (4) 2 hours at 42-65° in 1×SSC and 1% SDS, changing the solution every 30 minutes.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated Tm of the hybrid. Wash conditions should be as stringent as possible for the degree of identity of the probe for the target. In general, wash conditions are selected to be approximately 12-20° C. below the Tm of the hybrid. In regards to the nucleic acids of the current invention, a moderate stringency hybridization is defined as hybridization in 6×SSC, 5×Denhardt's solution, 0.5% SDS and 100 μg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 μg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 μg/ml denatured salmon sperm DNA at 42° C., and washed in 0.1× SSC and 0.5% SDS at 65° C. for 15 minutes.

The term "probe" as used herein refers to an oligonucleotide, polynucleotide or DNA molecule, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to a DNA oligonucleotide, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The terms "percent similarity", "percent identity" and "percent homology", when referring to a particular sequence are used as set forth in the University of Wisconsin GCG software program.

The term "functional" as used herein implies that the nucleic or amino acid sequence is functional for the recited assay or purpose.

"Natural allelic variants", "mutants" and "derivatives" of particular sequences of nucleic acids refer to nucleic acid sequences that are closely related to a particular sequence but which may possess, either naturally or by design, changes in sequence or structure. By closely related, it is meant that at least about 75%, but often, more than 90%, of the nucleotides of the sequence match over the defined length of the nucleic acid sequence referred to using a specific SEQ ID NO. Changes or differences in nucleotide sequence between closely related nucleic acid sequences may represent nucleotide changes in the sequence that arise during the course of normal replication or duplication in nature of the particular nucleic acid sequence. Other changes may be specifically designed and introduced into the sequence for specific purposes, such as to change an amino acid codon or sequence in a regulatory region of the nucleic acid. Such specific changes may be made in vitro using a variety of mutagenesis techniques or produced in a host organism placed under particular selection conditions that induce or select for the changes. Such sequence variants generated specifically may be referred to as "mutants" or "derivatives" of the original sequence.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the basic and novel characteristics of the sequence.

The term "promoters" or "promoter" as used herein can refer to a DNA sequence that is located adjacent to a DNA sequence that encodes a recombinant product. A promoter is preferably linked operatively to an adjacent DNA sequence. A promoter typically increases an amount of recombinant product expressed from a DNA sequence as compared to an amount of the expressed recombinant product when no promoter exists. A promoter from one organism can be utilized to enhance recombinant product expression from a DNA sequence that originates from another organism. For example, a vertebrate promoter may be used for the expression of jellyfish GFP in vertebrates. In addition, one promoter element can increase an amount of recombinant products expressed for multiple DNA sequences attached in tandem. Hence, one promoter element can enhance the expression of one or more recombinant products. Multiple promoter elements are well-known to persons of ordinary skill in the art.

The term "enhancers" or "enhancer" as used herein can refer to a DNA sequence that is located adjacent to the DNA sequence that encodes a recombinant product. Enhancer elements are typically located upstream of a promoter element or can be located downstream of or within a coding DNA sequence (e.g., a DNA sequence transcribed or translated into a recombinant product or products). Hence, an enhancer element can be located 100 base pairs, 200 base pairs, or 300 or more base pairs upstream or downstream of a DNA sequence that encodes recombinant product. Enhancer elements can increase an amount of recombinant product expressed from a DNA sequence above increased expression afforded by a promoter element. Multiple enhancer elements are readily available to persons of ordinary skill in the art.

The terms "transfected" and "transfection" as used herein refer to methods of delivering exogenous DNA into a cell. These methods involve a variety of techniques, such as treating cells with high concentrations of salt, an electric field, liposomes, polycationic micelles, or detergent, to render a host cell outer membrane or wall permeable to nucleic acid molecules of interest. These specified methods are not limiting and the invention relates to any transformation technique well known to a person of ordinary skill in the art.

A "replicon" is any genetic element, for example, a plasmid, cosmid, bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "oligonucleotide," as used herein refers to sequences, primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like).

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

The term "gene" refers to a nucleic acid comprising an open reading frame encoding a polypeptide, including both exon and (optionally) intron sequences. The nucleic acid may also optionally include non-coding sequences such as promoter or enhancer sequences. The term "intron" refers to a DNA sequence present in a given gene that is not translated into protein and is generally found between exons.

The phrase "operably linked," as used herein, may refer to a nucleic acid sequence placed into a functional relationship with another nucleic acid sequence. Examples of nucleic acid sequences that may be operably linked include, without limitation, promoters, cleavage sites, purification tags, transcription terminators, enhancers or activators and heterologous genes which when transcribed and translated will produce a functional product such as a protein, ribozyme or RNA molecule.

The phrase "solid support" refers to any solid surface including, without limitation, any chip (for example, silica-based, glass, or gold chip), glass slide, membrane, bead, solid particle (for example, agarose, sepharose, polystyrene or magnetic bead), column (or column material), test tube, or microtiter dish.

The phrases "affinity tag," "purification tag," and "epitope tag" may all refer to tags that can be used to effect the purification of a protein of interest. Purification/affinity/epitope tags are well known in the art (see Sambrook et al., 2001, Molecular Cloning, Cold Spring Harbor Laboratory) and include, but are not limited to: polyhistidine tags (e.g. 6×His), polyarginine tags, glutathione-S-transferase (GST), maltose binding protein (MBP), S-tag, influenza virus HA tag, thioredoxin, staphylococcal protein A tag, the FLAG™ epitope, AviTag epitope (for subsequent biotinylation), dihydrofolate reductase (DHFR), an antibody epitope (e.g., a sequence of amino acids recognized and bound by an antibody), and the c-myc epitope.

A "cell line" is a clone of a primary cell or cell population that is capable of stable growth in vitro for many generations.

An "immune response" signifies any reaction produced by an antigen, such as a viral antigen, in a host having a functioning immune system. Immune responses may be either humoral in nature, that is, involve production of immunoglobulins or antibodies, or cellular in nature, involving various types of B and T lymphocytes, dendritic cells, macrophages, antigen presenting cells and the like, or both. Immune responses may also involve the production or elaboration of various effector molecules such as cytokines, lymphokines and the like. Immune responses may be measured both in in vitro and in various cellular or animal systems. Such immune responses may be important in protecting the host from disease and may be used prophylactically and therapeutically.

An "antibody" or "antibody molecule" is any immunoglobulin, including antibodies and fragments thereof, that binds to a specific antigen. The term includes polyclonal, monoclonal, chimeric, single domain (Dab) and bispecific antibodies. As used herein, antibody or antibody molecule contemplates recombinantly generated intact immunoglobulin molecules and immunologically active portions of an immunoglobulin molecule such as, without limitation: Fab, Fab', F(ab')$_2$, F(v), scFv, scFv$_2$, scFv-Fc, minibody, diabody, tetrabody, single variable domain (e.g., variable heavy domain, variable light domain), bispecific, AFFIBODY® domain Z of *staphylococcus* protein A molecules (Affibody, Bromma, Sweden), and peptabodies (Terskikh et al. (1997) PNAS 94:1663-1668). Dabs can be composed of a single variable light or heavy chain domain. In a certain embodiment of the invention, the variable light domain and/or variable heavy domain specific for MISIIR are inserted into the backbone of the above mentioned antibody constructs. Methods for recombinantly producing antibodies are well-known in the art. For example, commercial vectors comprising constant genes to make IgGs from scFvs are provided by Lonza Biologics (Slough, United Kingdom).

"Fv" is an antibody fragment which contains an antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although often at a lower affinity than the entire binding site.

"Single-chain Fv" or "scFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv see, for example, Pluckthun, A. in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) on the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Holliger et al., (1993) Proc. Natl. Acad. Sci. USA, 90: 6444-6448.

With respect to antibodies, the term "immunologically specific" refers to antibodies that bind to one or more epitopes of a protein or compound of interest, but which do not substantially recognize and bind other molecules in a sample containing a mixed population of antigenic biological molecules.

As used herein, the term "immunotoxin" refers to chimeric molecules in which antibody molecules or fragments thereof are coupled or fused (i.e., expressed as a single polypeptide or fusion protein) to toxins or their subunits. Toxins to be conjugated or fused can be derived form various sources, such as plants, bacteria, animals, and humans or be synthetic toxins (drugs), and include, without limitation, saprin, ricin, abrin, ethidium bromide, diptheria toxin, *Pseudomonas* exotoxin, PE40, PE38, saporin, gelonin, RNAse, protein nucleic acids (PNAs), ribosome inactivating protein (RIP), type-1 or type-2, pokeweed anti-viral protein (PAP), bryodin, momordin, and bouganin.

The term "conjugated" refers to the joining by covalent or noncovalent means of two compounds or agents of the invention.

Chemotherapeutic agents are compounds that exhibit anti-cancer activity and/or are detrimental to a cell (e.g., a toxin). Suitable chemotherapeutic agents include, but are not limited to: toxins (e.g., saporin, ricin, abrin, ethidium bromide, diptheria toxin, *Pseudomonas* exotoxin, and others listed above; thereby generating an immunotoxin when conjugated or fused to an antibody); alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nitroso ureas such as carmustine, lomustine, and streptozocin; platinum complexes such as cisplatin and carboplatin; bioreductive alkylators such as mitomycin, procarbazine, dacarbazine and altretamine); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, vinblastine, and paclitaxel (TAXOL®)); hormonal agents (e.g., estrogens; conjugated estrogens; ethinyl estradiol; diethyistilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide). Preferably, the chemotheraputic agent is selected from the group consisting of: placitaxel TAXOL®), cisplatin, docetaxol, carboplatin, vincristine, vinblastine, methotrexate, cyclophosphamide, CPT-11, 5-fluorouracil (5-FU), gemcitabine, estramustine, carmustine, adriamycin (doxorubicin), etoposide, arsenic trioxide, irinotecan, and epothilone derivatives.

The term "pro-drug" refers to a compound which is transformed in vivo to an active form of the drug. The pro-drug may be transformed to an active form only upon reaching the target in vivo or upon internalization by the target cell.

Radioisotopes of the instant invention include, without limitation, positron-emitting isotopes and alpha-, beta-, gamma-, Auger- and low energy electron-emitters. The radioisotopes include, without limitation: $^{13}$N, $^{18}$F, $^{32}$P, $^{64}$Cu, $^{66}$Ga, $^{67}$Ga, $^{68}$Ga, $^{67}$Cu, $^{77}$Br, $^{80m}$Br, $^{82}$Rb, $^{86}$Y, $^{90}$Y, $^{95}$Ru, $^{97}$Ru, $^{99m}$Tc, $^{103}$Ru, $^{105}$Ru, $^{111}$In, $^{113m}$In, $^{113}$Sn, $^{121m}$Te, $^{122m}$Te, $^{125m}$Te, $^{123}$I, $^{124}$I, $^{125}$I, $^{126}$I, $^{131}$I, $^{133}$I, $^{165}$Tm, $^{167}$Tm, $^{168}$Tm, $^{177}$Lu, $^{186}$Re, $^{188}$Re, $^{195m}$Hg, $^{211}$At, $^{212}$Bi, $^{213}$Bi, and $^{225}$Ac. When the conjugated antibodies of the instant invention are employed for radio-immunodetection, the radioisotope is preferably a gamma-emitting isotope. When the conjugated antibodies of the instant invention are employed for detection by ImmunoPET (positron emission tomography), the radioisotope is preferably a positron-emitting isotope such as, without limitation, $^{13}$N, $^{18}$F, $^{82}$Rb. When the conjugated antibodies of the instant invention are employed for radioimmunotherapy (i.e., the treating of a patient with cancer), the radioisotope is preferably selected from the group consisting of $^{90}$Y, $^{131}$I, $^{177}$Lu, and $^{186}$Re, although other radionuclides such as many of those listed above are also suitable.

The term "radiosensitizer", as used herein, is defined as a molecule administered to animals in therapeutically effective amounts to increase the sensitivity of the cells to radiation. Radiosensitizers are known to increase the sensitivity of cancerous cells to the toxic effects of radiation. Radiosensitizers include, without limitation, 2-nitroimidazole compounds, and benzotriazine dioxide compounds, halogenated pyrimidines, metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

II. Preparation of Antibody Molecules

The antibody molecules of the invention may be prepared using a variety of methods known in the art. Polyclonal and monoclonal antibodies are prepared as described in Current Protocols in Molecular Biology, Ausubel et al. eds. Antibodies may be prepared by chemical cross-linking, hybrid hybridoma techniques and by expression of recombinant antibody fragments expressed in host cells, such as bacteria or yeast cells. Indeed, Salhi et al. describe the generation of an anti-MISIIR monoclonal antibody, 12G4, generated by a hybrid hybridoma technique (Biochem. J. (2004) 379:785-793).

In one embodiment of the invention, the antibody molecules are produced by expression of recombinant antibody fragments in host cells. The genes for several of the antibody molecules that target MISIIR have been cloned. The nucleic acid molecules encoding the MISIIR antibody fragments are inserted into expression vectors and introduced into host cells. The resulting antibody molecules are then isolated and purified from the expression system. The antibodies optionally comprise a purification tag by which the antibody can be purified.

The purity of the antibody molecules of the invention may be assessed using standard methods known to those of skill in the art, including, but not limited to, ELISA, immunohistochemistry, ion-exchange chromatography, affinity chromatography, immobilized metal affinity chromatography (IMAC), size exclusion chromatography, polyacrylamide gel electrophoresis (PAGE), western blotting, surface plasmon resonance and mass spectroscopy.

III. Uses of Anti-Misiir Antibody Molecules

Anti-MISIIR antibodies have broad applications in therapy and diagnosis. Specifically, the anti-MISIIR antibody molecules of the invention may be used: (1) to directly alter the growth of tumors that express MISIIR; (2) to alter the growth of tumors that express MISIIR in combination with other cytotoxic agents; (3) to image tumors that express MISIIR; and (4) as a diagnostic tool.

1) The anti-MISIIR antibody molecules of the instant invention can be administered to a patient in need thereof, as described hereinbelow. The anti-MISIIR antibody molecules of the instant invention include the antibodies alone and antibodies conjugated to other agents such as, without limitation, chemotherapeutic agents, radioisotopes, pro-drugs, pro-drug activating enzymes capable of converting a pro-drug to its active form, and magnetic beads (see, for example, U.S. Pat. No. 6,645,731). If the compound to be conjugated is proteinaceous, a fusion protein may be generated with the antibody molecule. Radiosensitizers may also be administered with the antibodies.

2) To alter the growth of tumors that express MISIIR, the anti-MISIIR antibody molecules of the instant invention may be administered to a patient in combination with other cytotoxic agents. These other cytotoxic agents include, without limitation, chemotherapeutic agents, external beam radiation, targeted radioisotopes, and other antibodies or signal transduction inhibitors. Radiosensitizers may also be administered with the antibodies.

3) When employed for imaging tumors, the anti-MISIIR antibody molecules of the invention can be conjugated to radioisotopes as described hereinabove. The anti-MISIIR antibody molecules can be conjugated to the radioisotopes by any method including direct conjugation and by linking through a chelator (see, for example, U.S. Pat. No. 4,624,846). The anti-MISIIR antibody molecules may also be conjugated to labels or contrast agents such as, without limitation, paramagnetic or superparamagnetic ions for detection by MRI imaging and optical and fluorescence and/or mammography agents (examples of other labels are provided in, for example, U.S. Pat. Nos. 3,817,837; 3,850,752; 3,939,350; 3,996,345; 4,277,437; 4,275,149 and 4,366,241). Paramagnetic ions include, without limitation, Gd(III), Eu(III), Dy(III), Pr(III), Pa(IV), Mn(II), Cr(III), Co(III), Fe(III), Cu(II), Ni(II), Ti(III), and V(IV). Fluorescent agents include, without limitation, fluorescein and rhodamine and their derivatives. Optical agents include, without limitation, derivatives of phorphyrins, anthraquinones, anthrapyrazoles, perylenequinones, xanthenes, cyanines, acridines, phenoxazines and phenothiazines. Mammography agents include, without limitation, derivatives of iodine or metals such as gold, gold particles or gold nanoparticles.

In an alternative method, a secondary binding ligand, such as a second antibody or a biotin/avidin ligand binding arrangement, which can recognize the anti-MISIIR antibody molecules of the instant invention, may be conjugated with the agents described above instead of with the anti-MISIIR antibody molecules. The conjugated secondary binding ligand can then be used in conjunction with anti-MISIIR antibody molecules in any of the assays described herein.

4) The anti-MISIIR antibody molecules of the invention may be used to 1) diagnose cancer in patient, 2) determine the prognosis of a patient, including stage and grade (particularly whether it is metastatic) of a tumor and its potential sensitivity to therapy, 3) determine the origin of a tumor, 4) determine the efficacy of a treatment of a patient. In one embodiment the anti-MISIIR antibody molecules are utilized to detect the presence of MISIIR in a biological sample from a patient. The biological sample may include biopsies of various tissues including, without limitation: breast, prostate, cervical, ovarian, testicular, and pulmonary. Cellular examples of biological samples include tumor cells, blood cells, ovarian cells, prostate cells, breast cells, testicular cells, cervical cells, and lung cells. The biological sample may also be a biological fluid, wherein shed MISIIR can be detected, such as, without limitation, blood, serum, nipple aspirate and urine. Many immunological assays are well known in the art for assaying of biological samples for the presence of a certain protein including, without limitation: immunoprecipitations, radioimmunoassays, enzyme-linked immunosorbent assays (ELISA), immunohistochemical assays, Western blot and the like.

The presence of MISIIR in fluids such as blood may be indicative of the presence of cancer. The presence of MISIIR in fluids or sites not near the tumor may be indicative of metastases. The loss of MISIIR expression in a patient, particularly one undergoing treatment, over time is indicative of remission (i.e., successful treatment) while the gain of MISIIR expression in a patient over time can be indicative of recurrence. Additionally, the imaging techniques described hereinabove may be employed to monitor the size of the tumor to determine the efficacy of a treatment. In a particular embodiment of the invention, other cancer diagnostic assays can be performed to confirm the results obtained with the instant invention.

The anti-MISIIR antibody molecules of the invention may also be used in gene therapy for direct targeting of vehicles (liposomes, viruses etc.) containing genes to specific tumors expressing MISIIR. In an exemplary embodiment, liposomes may be studded by the anti-MISIIR antibody molecules of the invention to facilitate tumor specific targeting. In another embodiment, anti-MISIIR antibodies may be expressed directly on the surface of viruses or as fusions with viral coat proteins to facilitate tumor specific targeting. The genes targeted in this manner can have a direct anti-tumor effect, sensitize the tumor to other agents or increase the susceptibility of the tumor to a host immune response. Anti-cancer agents such as chemotherapeutic agents, toxins, antibodies, antisense molecules, RNAi and/or radioisotopes may also be encapsulated in liposomes so modified.

In another embodiment, the anti-MISIIR antibody molecules may be used to direct gene therapy vectors, including but not limited to modified viruses, to cells that express MISIIR. Viruses and other vectors may also be utilized to deliver the genes for the anti-MISIIR antibody molecules to tumor cells where they could be produced and secreted into the cellular microenvironment or, through the addition of additional intracellular targeting sequences, they could be turned into intrabodies that localize to specific cellular compartments and knockout the expression of their targets.

In yet another embodiment of the instant invention, the anti-MISIIR antibody molecules of the instant invention can be conjugated or covalently attached to another targeting agent to increase the specificity of the tumor targeting. Targeting agents can include, without limitation, antibodies, cytokines, and receptor ligands. In a particular embodiment, the targeting agent is overexpressed on the tumor as compared to normal tissue. Additionally, the anti-MISIIR antibody molecules of the instant invention can be conjugated or covalently attached to compounds which elicit an immune response such as, without limitation, cytokines.

The present invention further encompasses kits for use in detecting the expression of MISIIR in biological samples. Such kits may comprise the anti-MISIIR antibody molecules of the invention specific for MISIIR as well as buffers and other compositions and instruction material to be used for the detection of the MISIIR.

IV. Administration of Antibodies

The antibodies as described herein will generally be administered to a patient as a pharmaceutical preparation. The term "patient" as used herein refers to human or animal subjects. These antibodies may be employed therapeutically, under the guidance of a physician for the treatment of malignant tumors and metastatic disease.

The pharmaceutical preparation comprising the antibody molecules of the invention may be conveniently formulated for administration with an acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of antibody molecules in the chosen medium will depend on the hydrophobic or hydrophilic nature of the medium, as well as the size and other properties of the antibody molecules. Solubility limits may be easily determined by one skilled in the art.

As used herein, "biologically acceptable medium" includes any and all solvents, dispersion media and the like which may be appropriate for the desired route of administration of the pharmaceutical preparation, as exemplified in the preceding paragraph. The use of such media for pharmaceutically active substances is known in the art. Except insofar as any conventional media or agent is incompatible with the antibody molecules to be administered, its use in the pharmaceutical preparation is contemplated.

The dose and dosage regimen of an antibody according to the invention that is suitable for administration to a particular patient may be determined by a physician considering the patient's age, sex, weight, general medical condition, and the specific condition and severity thereof for which the antibody is being administered. The physician may also consider the route of administration of the antibody, the pharmaceutical carrier with which the antibody may be combined, and the antibody's biological activity.

Selection of a suitable pharmaceutical preparation depends upon the method of administration chosen. For example, the antibodies of the invention may be administered by direct injection into any cancerous tissue or into the surrounding area. In this instance, a pharmaceutical preparation comprises the antibody molecules dispersed in a medium that is compatible with the cancerous tissue.

Antibodies may also be administered parenterally by intravenous injection into the blood stream, or by subcutaneous, intramuscular or intraperitoneal injection. Pharmaceutical preparations for parenteral injection are known in the art. If parenteral injection is selected as a method for administering the antibodies, steps must be taken to ensure that sufficient amounts of the molecules reach their target cells to exert a biological effect. The lipophilicity of the antibodies, or the pharmaceutical preparation in which they are delivered, may have to be increased so that the molecules can arrive at their target locations. Furthermore, the antibodies may have to be delivered in a cell-targeting carrier so that sufficient numbers of molecules will reach the target cells. Methods for increasing the lipophilicity of a molecule are known in the art. If a small form of the antibody is to be administered, including but not limited to a Fab fragment, a Dab, an scFv or a diabody, it may be conjugated to a second molecule such as, but not limited to polyethylene glycol (PEG) or an albumin-binding antibody or peptide to prolong its retention in blood.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the antibody in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of anti-MISIIR antibody molecules may be determined by evaluating the toxicity of the antibody molecules in animal models. Various concentrations of antibody pharmaceutical preparations may be administered to mice with transplanted human tumors, and the minimal and maximal dosages may be determined based on the results of significant reduction of tumor size and side effects as a result of the treatment. Appropriate dosage unit may also be determined by assessing the efficacy of the antibody molecule treatment in combination with other standard anti-cancer drugs. The dosage units of anti-MISIIR antibody molecules may be determined individually or in combination with each anti-cancer treatment according to greater shrinkage and/or reduced growth rate of tumors.

The pharmaceutical preparation comprising the anti-MISIIR antibody molecules may be administered at appropriate intervals, for example, at least twice a day or more until the pathological symptoms are reduced or alleviated, after which the dosage may be reduced to a maintenance level. The appropriate interval in a particular case would normally depend on the condition of the patient.

The following examples provide illustrative methods of practicing the instant invention, and are not intended to limit the scope of the invention in any way. While certain of the following examples specifically recite a certain type of anti-MISIIR antibody (e.g., scFv and diabody), the use of any anti-MISIIR antibody is within the scope of the instant invention. Additionally, while radioisotope conjugated antibodies are also exemplified, immunotoxins may also be employed for therapeutic purposes.

EXAMPLE 1

Identification of MISIIR Specific Antibodies

Single-chain Fv (scFv) molecules specific for MISIIR were obtained by employing a panning (selection) strategy of a human scFv combinatorial phage display library similar to that employed for identifying scFv molecules specific for Her2/neu (Horak, E. M., et al. (2001) Proc. Amer. Assoc. Cancer Res., 39:774). Specifically, the MSIIR gene was isolated by performing RT-PCR on a human testicle Poly (A) RNA library (Cat #7973; Ambion; Austin, Tex.). The portion of the resulting cDNA encoding the ECD (extracellular domain) of MISIIR (FIG. 7) was cloned into the pSecTag2/Hygro vector (Invitrogen, Carlsbad, Calif.) which encodes for a 6×His tag and a c-myc tag to be added to the carboxyl-terminus of the protein and a secretion signal to be added to the amino-terminus. The DNA encoding for the ECD of MISIIR was inserted in to the vector in two orientations, either 5' or 3' of a human IgG1 Fc domain in order to facilitate secretion of the fully folded MISIIR into the supernatant. A tobacco etch virus cleavage site was engineered into the construct between MISIIR and the Fc domain to facilitate the separation of the final product from the Fc domain.

Figure 1:
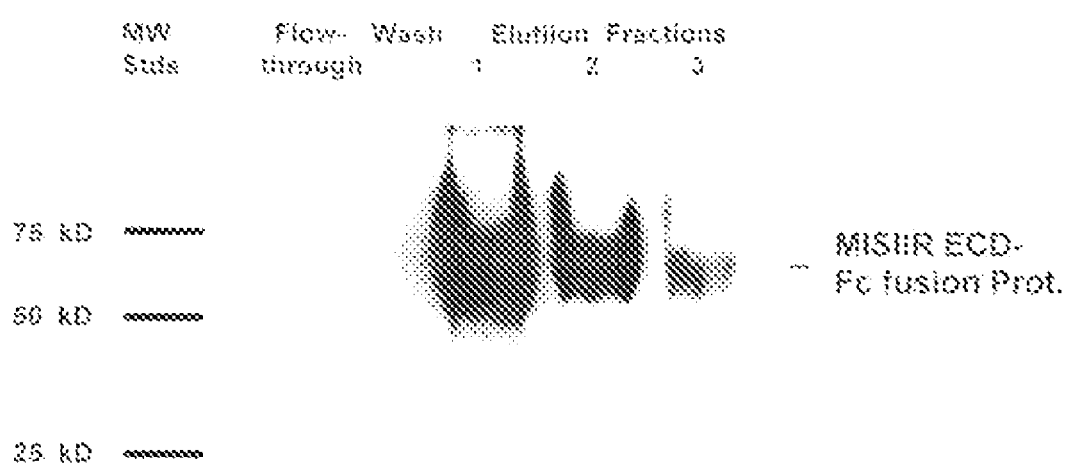

HEK 293 cells, grown in serum-free media, were stably transfected with both constructs and each fusion protein was isolated from culture supernatants by immobilized metal affinity chromatography; IMAC (Hochuli, E., et al. (1988) Bio/Technology, 6:1321-1325). A western blot of the protein expressed from the construct encoding for the ECD of MISIIR 5' of the Fc domain is shown in FIG. 1. The purified fusion protein was coated onto the sides of a Nunc-Immuno™ tube (Nalge Nunc; Rochester, N.Y.). A human scFv combinatorial phage display library consisting of $10^{11}$ unique scFv clones (provided by Wayne Marasco, Dana-Farber Cancer Institute) was mixed with 100-fold excess of human IgG Fc domain and subsequently added to the Nunc-Immuno™ tube. The premixing of the library with a large excess of Fc domain diminished the likelihood that phage expressing anti-Fc scFv would bind the immobilized MISIIR-Fc fusion protein. Selection of phage displaying anti-MISIIR scFv molecules was performed similarly to the method described in Adams and Schier (Adams, G. P. and Schier, R. (2000) Methods in Molecular Medicine Vol. 39: Ovarian Cancer. Ed. Bartlett, J. The Humana Press, Totowa, N.J., pp. 729-747). Briefly, the Nunc-Immuno™ tube containing the phage library and excess Fc domain was washed and reactive phage were eluted by the addition of 100 mM triethylamine. TG1 E. coli were challenged with the eluted phage. Subsequently, phage particles were isolated from the infected bacteria and employed in subsequent rounds of binding and selecting.

After three rounds of selection, 200 phage-scFv clones were randomly isolated from the selection plates containing thousands of colonies. The clones were expanded and assayed by ELISA for binding to MISIIR-Fc and to IgG Fc domain. Thirty-three clones exhibited significant specificity for MISIIR-Fc without any evidence for specificity for IgG Fc domain.

Figure 2:
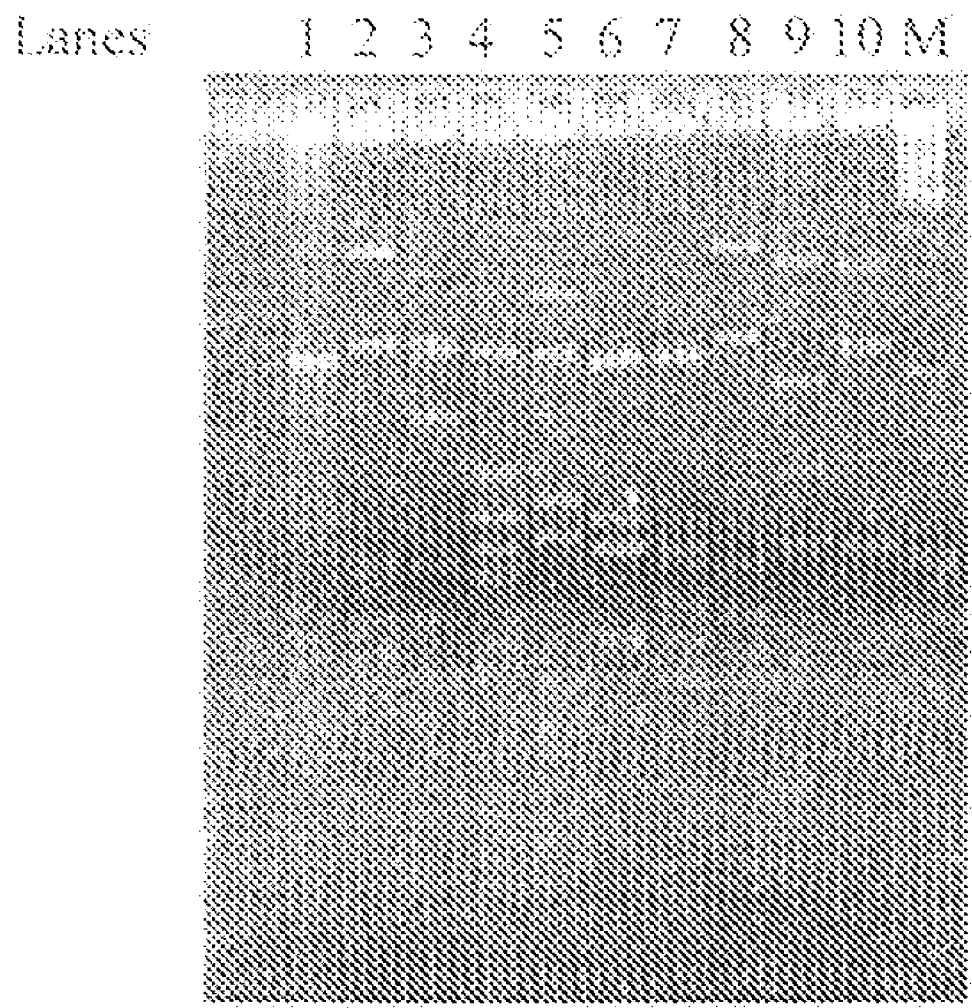

After isolation of the vector containing the scFv gene from the 33 phage clones by phenol chloroform extraction, a PCR fingerprinting assay was performed. Briefly, the PCR fingerprinting assay entailed digesting the isolated scFv gene with BstN1 at 60° C. for 2 hours and analyzing the restriction pattern on an agarose gel. As exemplified in FIG. 2, 16 of the clones had different restriction patterns and therefore contained scFv genes of unique nucleotide sequences.

Figure 3:
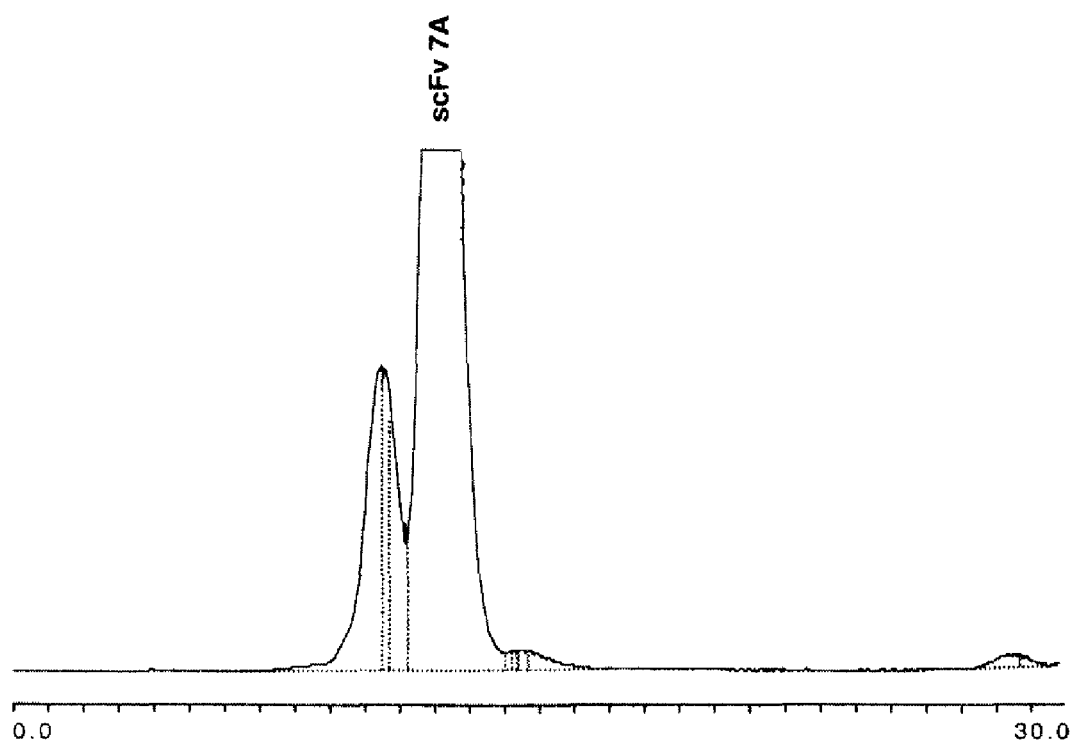
Figure 4:
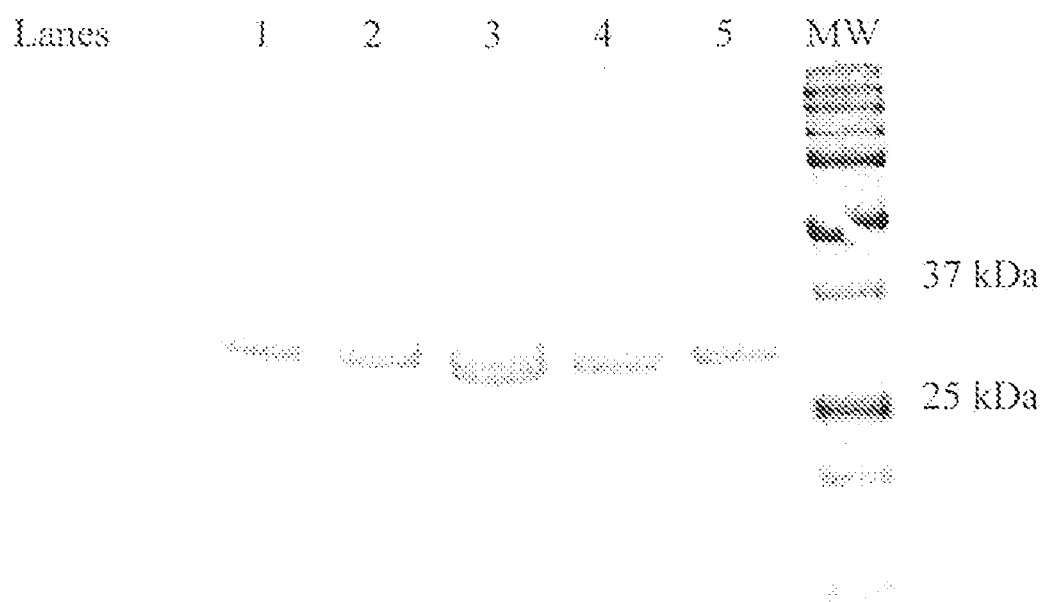

DNA sequencing of the clones determined to be unique by PCR fingerprinting revealed that 12 of the 16 clones possessed unique amino acid sequences. All 12 unique clones were transferred into the pCYN expression vector (also referred to as pUC119mychis), expressed in E. coli with induction by the addition of isopropyl-β-D-thioglactopyranoside (IPTG), and then purified by IMAC (Schier, R., et al. (1995) Immunotechnology, 1:73-81; Adams, G. P., et al. (2000) Methods in Molecular Medicine Vol. 39:Ovarian Cancer, The Humana Press: Totowa, N.J., 729-747). The protein eluted from the resin was further purified by size exclusion chromatography using HPLC (high performance liquid chromatography) on a Superdex™ 75 column (Amersham; Piscataway, N.J.) (FIG. 3). The elution pattern indicated that anti-MISIIR scFv from clone #7A is primarily monomeric. 2.5 mg of purified anti-MISIIR scFv from clone #7A (major peak in FIG. 3) was obtained from 1 liter of bacterial culture. Polyacrylamide gel electrophoresis analysis of the elution fractions from the size exclusion chromatography demonstrated the sequential purification scheme resulted in highly purified product (FIG. 4).

Figure 5:
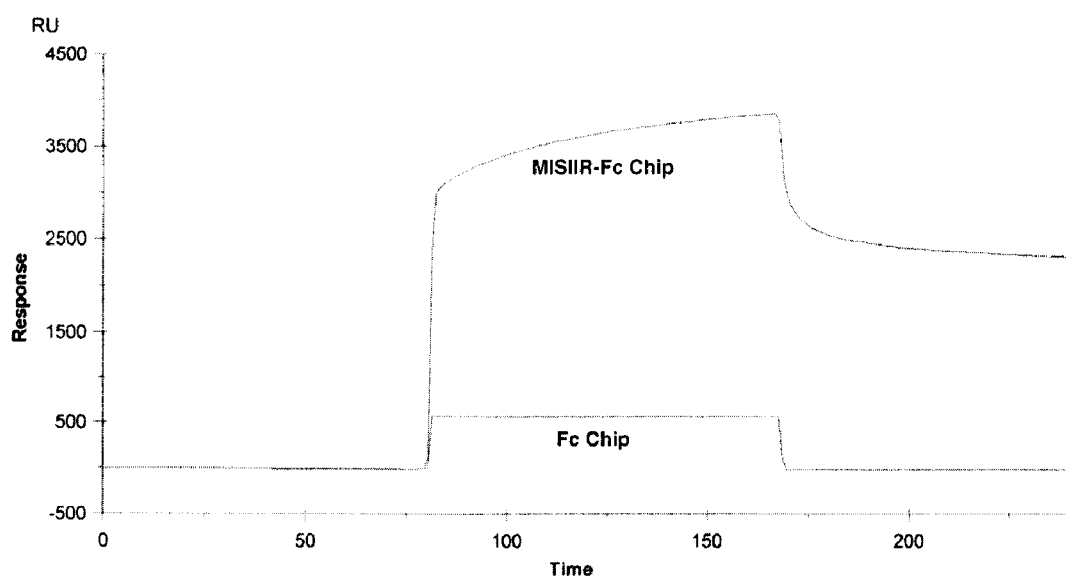
FIG. 5 is a graph of the surface plasmon resonance assay performed with anti-MISIIR scFv (clone #17). MISIIR-Fc and IgG Fc were immobilized on a BIACORE® chip.

All 12 purified scFv molecules were also evaluated by surface plasmon resonance on a BIACORE® (Uppsala, Sweden) surface plasmon resonance instrument to determine the ability of the scFv molecules to bind highly purified MISIIR ECD. Surface plasmon resonance analysis revealed that at least 7 of the 12 scFv molecules bind to MISIIR-Fc but not to IgG alone (see, e.g., clone #17 (FIG. 8), which displayed a high affinity for the ECD of MISIIR, in FIG. 5). As seen in FIG. 5, the dissociation rate of scFv from MISIIR-Fc is slow, therefore indicating a strong interaction between the antibody and MISIIR. Such a strong interaction will allow for more durable retention of the antibody to a tumor expressing MISIIR.

The nucleotide sequences of certain scFv clones which displayed specific binding to MISIIR are provided in FIGS. 8-11, 14, 15 and 16 (SEQ ID NOs 1-7).

Figure 12A:
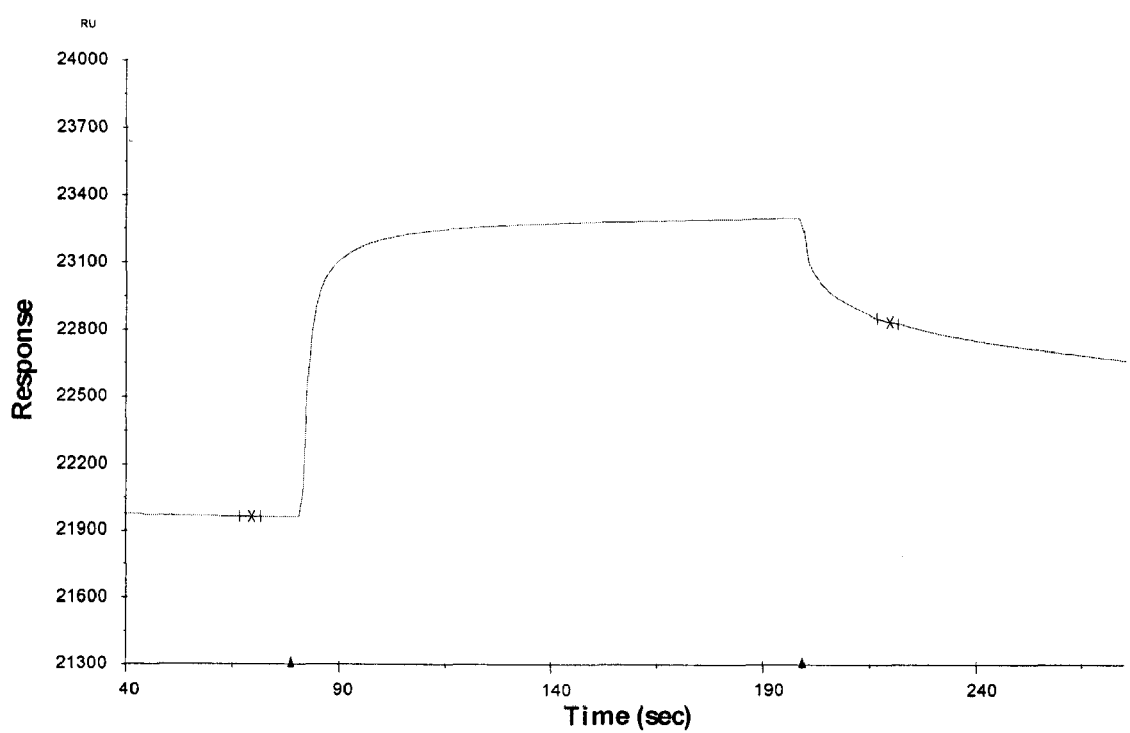
FIG. 12A and 12B are graphs of the surface plasmon resonance of a diabody of clone #17 and an scFv-Fc of clone #7, respectively, on a BIACORE® chip coated with MISIIR.
Figure 12B:
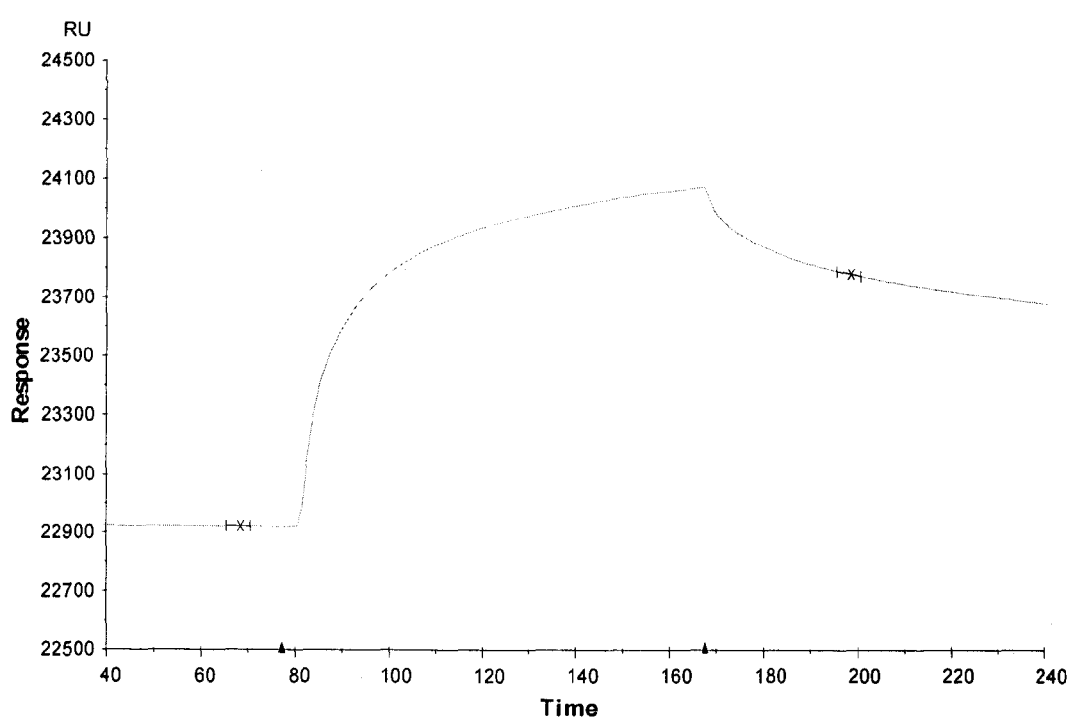

Surface plasmon resonance (SPR) technology was used to determine the binding of the anti-MISIIR molecules to MISIIR ECD. The SPR response reflects a change in the mass concentration as molecules bind or dissociate from an antigen immobilized on a sensor chip. These studies were performed on a BIACORE® 1000 surface plasmon resonance instrument. The MISIIR-Fc ECD fusion protein target antigen was coated on a CM5 chip at a concentration of 5,000 resonance units (RU). The anti-MISIIR antibody molecules were then flowed over the chip and the difference in the response units (RU) between the start point and the end was determined. A negative control protein (Fc) was coated on a chip at 4,800 RU and was used to rule out binding to the Fc portion of the MISIIR-Fc fusion protein. The association and dissociation rates, and the affinity of each molecule for MISIIR ECD were determined by passing serially diluted samples over an MISIIR-Fc ECD coated chip with a lower concentration of target antigen (600 RU) as per the BIACORE® surface plasmon resonance instrument manufacturer's instructions. The evaluation of the data was done using BIAEvaluation 3.0 software. FIG. 12A shows the SPR of a diabody of clone #17 and FIG. 12B shows the SPR of an scFv-Fc of clone #7. Additionally, an scFv of clone #7 and an scFv of clone #17 demonstrated an affinity for MISIIR ECD by SPR of $3 \times 10^{-7}$ M and $0.9 \times 10^{-7}$ M, respectively.

Figure 13:
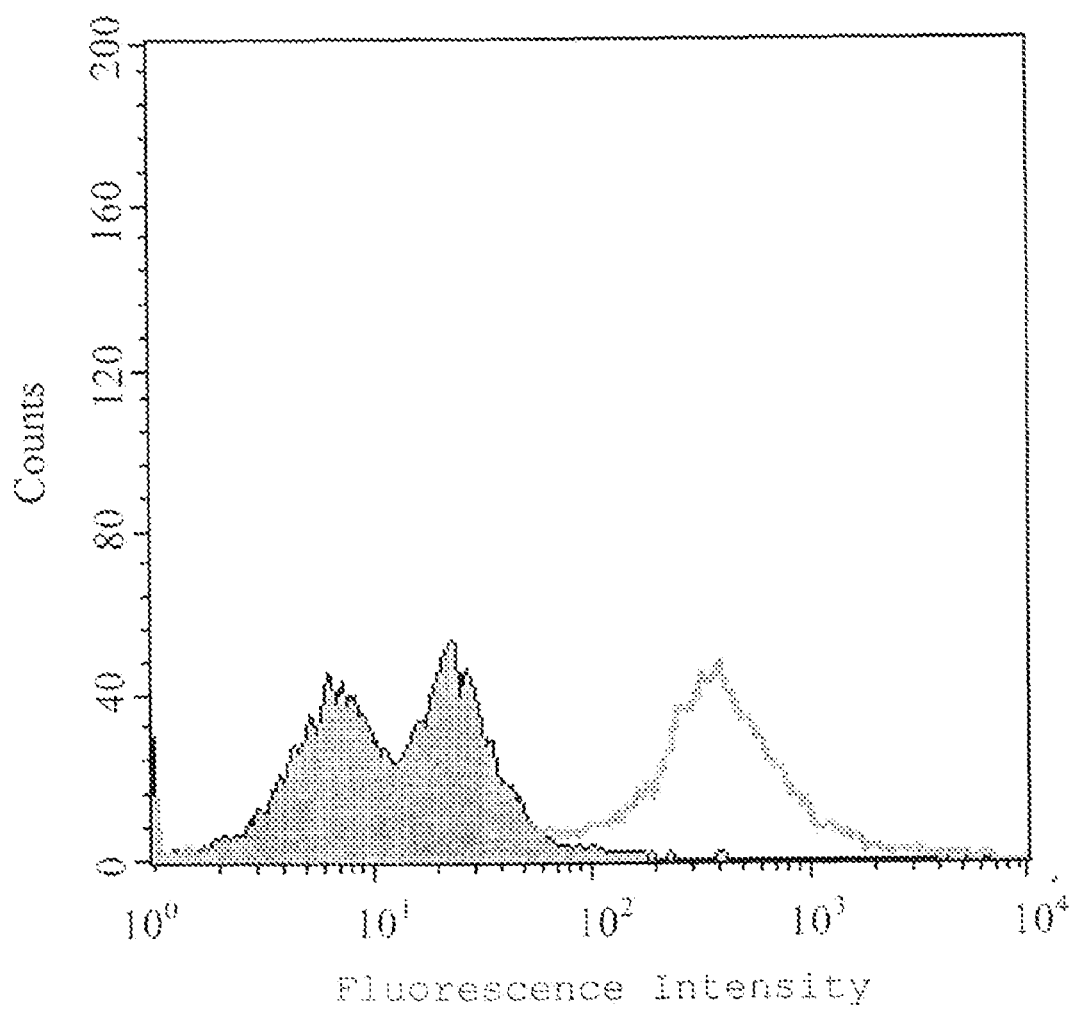
FIG. 13 is a graph of the binding of an scFv-Fc of clone #7 against IGROV-1 cells. The filled in results are a control IgG.

The binding of the antibodies was also tested in a standard fluorescence-activated cell sorter (FACS) assay. IGROV-1 cells, which express MISIIR, were analyzed for binding to an scFv-Fc of clone #7 and a control IgG. Binding of the scFv-Fc to the cells was detected with a fluorescin conjugated goat anti-human IgG (Catalog #AHI0408; Biosource International, Camarillo, Calif.). FIG. 13 demonstrates specific binding of the scFv-Fc of clone #7 for the MISIIR expressing IGROV-1 cells.

EXAMPLE 2

Identification of MISIIR Antibodies with Cytotoxic or Anti-Proliferative Effects MIS has been reported to exhibit antiproliferative effects in many ovarian cancer cell lines (Masiakos, P. T., et al. (1999) Clin. Cancer Res., 5:3488-3499). Accordingly, some anti-MISIIR scFv molecules can be expected to exhibit similar antagonistic effects. Therefore, the isolated unique anti-MISIIR scFv molecules identified in Example 1 can be evaluated for antiproliferative and pro-apoptotic effects on ovarian tumor cells that overexpress MISIIR and on control cells that lack MISIIR. Notably, scFv molecules bind to antigen monovalently, but engineered antibody-based molecules may also bind divalently. Therefore, scFv molecules can also be assayed as divalent antibodies in each of the assays described herein by contacting the anti-MISIIR scFv molecules with an anti-myc antibody such as 9E10 antibody (Santa Cruz Biotechnology; Santa Cruz, Calif.). Inasmuch as the anti-MISIIR scFv molecules contain a myc tag expressed on the carboxyl terminus, the presence of the anti-myc antibodies generates dimeric MISIIR binders. Additionally, recombinant MIS or purified MIS can be included in each assay as a positive control.

An example of an assay that may be employed to determine the effects of the anti-MISIIR scFv molecules on the growth and viability of cells is an MTT (3-[4,5-dimethylthiazol-2-yl]-2,5-diphenyl-tetrazolium bromide) assay (see, e.g., Sigma, St. Louis, Mo.). Briefly, living cells are able to metabolize MTT and the reaction product can be monitored colormetrically. The MTT assay may be performed as previously described wherein the purified anti-MISIIR scFv molecules are employed over a wide range of dilutions (e.g., ranging from 1 µM to 20 pM) in order to identify optimal doses (Amoroso, A. R., et al. (1996) Cancer Research, 56:113-120).

scFv clones that inhibit the proliferation of cell lines that express MISIIR (e.g., OVCAR-3, SK-OV-3, IGROV-1, and MOVAR) without altering the growth of cell lines that lack MISIIR (e.g., COS cells) then will be assayed in clonogenicity assays designed to evaluate their ability to induce cytotoxicity of the cell lines (Connolly, D. C., et al. (2003) Cancer Res., 1389-1397). Briefly, SK-OV-3, OVCAR-3, IGROV-1, MOVCAR and COS cells can be plated at a low concentration in tissue culture plates in fresh media or conditioned media in the presence of increasing concentrations of anti-MISIIR scFv. The cells can then be grown for one week at 37° C. Colonies can then be stained with, for example, 0.25% Methylene Blue in 30% ethanol and the number of colonies present in the treated plates can be compared to those in untreated plates. Once a response curve is determined, assays can be repeated with the addition of increasing doses of gamma irradiation using, for example, a cesium irradiator system in order to look for additive or synergistic effects of the anti-MISIIR scFvs and radiation. As noted above, the assays can be performed using both monovalent anti-MISIIR scFv and anti-MISIIR scFv that have been crosslinked with the anti-myc tag 9E10 MAb.

The anti-MISIIR scFv molecules that mediate cytotoxic effects in the clonogenicity assays can also be evaluated for the ability to induce apoptosis in cells that overexpress MISIIR. As an example, an ELISA assay can be performed to detect the translocation of phosphatidylserine from the inner face of the plasma membrane to the cell surface, which is associated with early apoptotic events. These assays can be performed using, for example, the ApoAlert™ Annexin V Apoptosis Kit (Clontech, Palo Alto, Calif.), which employs an ELISA assay based upon the high affinity of annexin V for phosphatidylserine. Briefly, at various times after incubation with anti-MISIIR scFv, MISIIR positive and negative cells can be washed, incubated with the annexin V-FITC conjugate, and evaluated in a microtiter plate reader. As above, the specificity of the results can be based upon the observation of a positive signal in the wells containing, for example, SK-OV-3, OVCAR-3, and possibly MOVCAR cells (depending upon epitope conservation) and no change in the signal in the wells containing negative controls such as COS cells which lack MISIIR. Alternatively, TUNEL (terminal deoxynucleotidyl transferase mediated dUTP-biotin nick end-labeling) assays can be performed on target and control cells after 24 hrs in the presence or absence of anti-MISIIR scFv (Surh, C. D. and Sprent, J. N. (1994) Nature, 372:100-103).

EXAMPLE 3

Diabody and scFv-Fc Construction

Diabodies can be created from the anti-MISIIR scFv genes using, for example, the same techniques as employed to create the anti-HER2/neu diabody from the C6.5 scFv (Adams, G. P. et al. (1998) British J. Cancer, 77:1405-1412). Diabodies can be generated from the scFv clones that had the greatest affect on the growth/survival properties of tumor cells and from clones that did not alter these characteristics as controls. As described, each diabody will be composed of two identical homodimers, but bispecific heterdiabodies can also be prepared. Briefly, the $V_H$ and $V_L$ genes from each selected scFv can be amplified from the scFv DNA and gel purified.

The $V_H$ and $V_L$ genes can be joined together by, for example, PCR splicing by overlap extension using an oligonucleotide which encodes a 5 amino acid linker ($G_4S$) between the C-terminus of the $V_H$ and the N-terminus of the $V_L$. Indeed, the diabody of clone #17 was generated with this G4S linker. The primer employed to amplify the variable heavy gene from the 3' end encoded for three extra glycines and contained a BamHI site. The primer employed to amplify the variable light gene from the 5' end contained a BamHI site. Notably, the BamHI site introduced a glycine-serine sequence into the encoded sequence for the antibody when the PCR fragments were ligated together, thereby resulting in the G4S linker.

The diabody gene can be cloned into a vector such as pUC119 Sfi-NotmycHis (Adams, G. P., et al. (1998) British J. Cancer, 77:1405-1412), resulting in the addition of the myc peptide tag (Schier, R., et al. (1995) Immunotechnology, 1:73-81) followed by a hexa-histidine tag at the C-terminal end of the diabody. The vector also encodes the pectate lyase leader sequence, which directs expression of the diabody into the bacterial periplasm where the leader sequence is cleaved. This makes it possible to harvest native properly folded diabody directly from the bacterial periplasm. Native diabody can be expressed and purified from the bacterial periplasm using, for example, immobilized metal affinity chromatography (IMAC) followed by FPLC size exclusion chromatography using a Superdex 75 column (Breitling, S. D., et al. (1991) Gene 104:147-153; Hochuli, E., et al. (1998) Bio/Technology, 6:1321-1325). Each diabody can be assayed as described above for the scFv molecules to determine the ability of each diabody to alter the growth properties of cells that overexpress MISIIR.

The scFv-Fc of clone #7 was generated using the hinge stuffer vector system (see, for example, www.nfcr-ctae.org). Briefly, the hinge stuffer vector is a pcDNA3.1 based plasmid in which a chimeric human F105 VH leader sequence (with 3' pelB leader) and human IgG1 sequence (hinge, CH2 and CH3 domains) flank SfiI (5') and Not1 (3') cloning sites that contain stuffer DNA (circa 439 bp). Upon digestion of the plasmid with SfiI and NotI restriction enzymes, the stuffer DNA drops out and the scFv fragments with identical restriction sites are cloned in frame. In this way, the bivalent human sFv-IgG fusion proteins are expressed and secreted from mammalian cells.

EXAMPLE 4

In Vivo Distribution Assays

Diabodies generated in Example 3 can be radiolabeled with $^{125}$I and tested for their ability to target human ovarian carcinoma xenografts growing in immunodeficient mice. Notably, $^{111}$In, among other isotopes, can be used in place of $^{125}$I, particularly if radioiodine labeled diabodies are rapidly internalized. In particular, in vivo biodistribution and pharmacokinetics can be determined and cumulative tumor:organ ratios can be calculated. These values can be used in MIRD (Medical Internal Radiation Dose) dosimetry calculations to determine the potential dose that would be achieved with the therapeutic isotopes $^{131}$I and $^{90}$Y in place of $^{125}$I. Such assays can be performed in SCID mice as previously described (Adams, G. P., et al. (1993) Cancer Res., 53:4026-4034). Briefly, groups of mice can receive intravenous (i.v.) injections of radioiodinated diabody and blood samples can be collected serially by retro-orbital bleeding at, for example, 5, 15, 30, 45 minutes, 1, 2, 4, 8, 16, 24, 48 and 72 hours post administration. The quantity of radioisotope retained per ml of blood can be determined. Trichloracetic acid (TCA) precipitation assays (Adams, G. P., et al. (1995) J. Nucl. Med., 36:2276-2281) can be performed to differentiate between protein-associated and unassociated counts to ensure that the distribution of the diabody is being followed. The pharmacokinetics can then be determined by analysis using the Rstrip program (Micromath, Salt Lake City, Utah). Biodistribution studies can also be performed similarly except that the SCID mice will also bear established subcutaneous 100-200 mm$^3$ tumors, such as OVCAR-3 or SK-OV-3 tumors, that overexpress MISIIR (Masiakos, P. T., et al. (1999) 5:3488-3499). AUC (area under the curve) calculations can then be determined from % ID (injected dose)/g values using, for example, the NCOMP program (Laub, P. and J. Gallo (1996) J. Pharm. Sci., 85:393-395).

Dose estimates for radiolabeled antibodies in humans can be calculated using mouse biodistribution data from the same molecule based upon the following assumptions: 1) tumor and normal organ concentration data in the mouse can be extrapolated to "reference man"; 2) the pharmacokinetics and biodistribution of $^{111}$Indium-radiolabeled antibody are equal to those of antibodies radiolabeled with $^{90}$Yttrium; and 3) the residence time of the radiopharmaceutical in tumors and organs in man is the same as that in the animal model. Finally, the S values (indicator of the radioactive doses that are both absorbed and emitted by a given organ; see MIRD program) for the mouse organs must be normalized to the human organs based upon the size of the organ relative to the whole animal versus the size of the organ relative to the whole person.

All dose estimates can be calculated based on Formula A ($[RT/PIDRB]_{man}$=$[RT/PIDRB]_{mouse}$) where RT=AUC/Activity administered and PIDRB=Percent Injected Dose Remaining in the Body. The computer program MIRD DOSE 3 (supplied by Oak Ridge Associated Universities) can be used to calculate radiation absorbed doses to all the organs in "reference man" based on the residence times established in the above equation. Since there are no S values available for tumors, the dose to tumor can be calculated based on separating the dose contributed by β particles and photons (Formula B: dose from β particles=$D_{np}$=([0.408 g cGy/μCi h]/[Tumor mass (g)])×Accumulated Activity (μCi h)). The dose from photons ($D_p$) can be counted equivalent to fraction of total body dose calculated for photons only ($D_{tumor}$=$D_{np}$+$D_p$). Molecules can be selected for evaluation in preclinical therapy trials based upon predicted human dosimetry from the MIRD calculations and tumor:normal organ AUC ratios. Preferably, diabodies will exhibit highly specific tumor targeting, e.g., a 3:1 ratio of cumulative tumor:normal dosimetry. Particular emphasis can be placed upon the $LD_{50}$ values for myelosuppression-sensitive organs such as the bone marrow (200-300 cGy) and those believed to be involved in the catabolism of the radiolabeled protein such as the kidneys (1500 cGy) and liver (4000 cGy). Diabodies selected for therapy studies can have predicted delivery of more than 4000 cGy to tumor, with an associated normal organ dose limit of less than 200 cGy for the bone marrow, 1200 cGy for kidneys and 3000 cGy to the liver (Murray, J., et al. (1994) Cancer, 73:1057-1066).

EXAMPLE 5

Imaging Studies

Ovarian cancers poses unique challenges for early detection and in monitoring responses to therapy (Ozols, R. F., et al. (2001) Cancer: Principles and Practice of Oncology, Lippincott Williams and Wilkins: Philadelphia, Pa.). CA-125 antigen detection in the circulating blood has proven useful in assessing the overall benefits of surgery or chemotherapy (Skates, S. J., et al. (2000) Methods in Molecular Medicine Vol. 39: Ovarian Cancer, The Humana Press: Totowa, N.J.). Non-invasive imaging by CT scanning, however, is insufficiently sensitive or specific to assess the impact of surgery or identify sites of tumor progression or regression. Antibody-based imaging of ovarian cancer has employed a variety of antibodies and radionuclide pairs (Kalofonos, H. P., et al. (1999) Acta Oncologica, 38:629-634), but none of these approaches has emerged as being sufficiently sensitive and specific for routine use.

The utility of using an anti-MISIIR diabody as a vehicle for the detection of ovarian cancer can be compared with the images obtained using the current PET imaging agent $^{18}$FDG ($^{18}$F fluorodeoxyglucose). An example of an assay for testing the sensitivity of the anti-MISIIR diabodies for this purpose is as follows.

Due to the significantly longer physical half-life of $^{124}$I, $^{18}$FDG imaging can be performed before $^{124}$I-conjugated diabody imaging studies. Immunodeficient mice bearing established 300 mm$^3$ subcutaneous (s.c.) human SK-OV-3 or OVCAR-3 ovarian carcinoma tumors can be administered 50 µCi of $^{18}$FDG by i.v. tail vein injection. At one and two hours after injection, the mice can be anesthetized and imaged on a Discovery™ LS PET/CT camera (GE Medical Systems; Waukesha, Wis.). Twenty four hours later, the diabody that is determined to be associated with the greatest degree of tumor targeting specificity in the biodistribution/dosimetry studies described above can be labeled with $^{124}$I, a positron-emitting radioisotope with a 4 day half-life) using the Chloramine T method. Notably, $^{64}$Cu, among other isotopes, can be used in place of $^{124}$I for imaging studies, particularly if the radioiodine-labeled diabodies are rapidly internalized. The $^{124}$I-conjugated diabody (50 microCuries on 50 micrograms of diabody per mouse) can be administered by i.v. tail vein injection and the mice can be anesthetized as described above. The mice can be imaged at, for example, 4, 12, 24, 36 and 48 hours post administration. Imaging can be performed, for example, on the Discovery™ LS Whole Body PET/CT Scanner (GE Medical Systems) or microPET®(Concorde Instruments; Knoxville, Tenn.).

The standard clinical PET/CT acquisition protocol may be significantly modified for murine imaging. A custom-designed platform can be mounted on to the edge of imaging table for imaging up to 3 mice simultaneously. The current setting for CT (computed tomography) can be reduced to 50 mAs and PET data can be acquired in 2D mode for 10 minutes. PET images can be reconstructed using a standard manufacturer supplied OSEM algorithm with 28 subsets and 2 iterations, with a reduced display field of view of 30 cm diameter, in a 256×256 matrix. CT can be used for applying attenuation correction. PET activity data can be corrected for radioactive decay and normalized for the dose administered. Additional CT images can also be acquired with a slice thickness of 1 mm. Images can be reviewed on an ENTEGRA™ work station (GE Medical Systems) as 3-D volume sets with simultaneous display of transverse, coronal and sagittal panes. Regions of interest (ROI's) can be drawn by two independent observers around tumors using a combination of PET and CT information to identify tumor edges. Both the maximum and average tumor activity concentration can be determined for any observed tumors from PET images. The size of the tumor can be estimated from CT images and activity can be corrected for object size effect using an experimentally determined recovery coefficient measured from mouse phantom studies with $^{124}$I.

The specificity of anti-MISIIR diabodies, degree of tumor targeting and retention as compared to normal tissue, and estimation of tumor and normal tissue dosimetry associated with radiolabeled anti-MISIIR diabodies can also be determined in humans. An example of such a study follows.

Women with metastatic, measurable MISIIR expressing ovarian cancer can be eligible for this study. MISIIR expression can be determined by IHC (immunohistochemistry) on archived biopsy or aspirate specimens (Garcia de Palazzo, I., et al. (1993) Intl. J. Biol. Markers, 8:233-239; Weiner, L. M., et al. (1995) Cancer Res., 55:4586-4593). Eligible patients should have acceptable normal organ function and should provide written informed consent. Prior antibody therapy can be permissible provided that at least two months have elapsed from the last antibody infusion.

On Day One, patients can receive an intravenous injection of 10 mCi of $^{18}$FDG. One hour later, PET/CT fusion images will be acquired using a Discovery™ LS PET/CT instrument (GE Medical Systems) or equivalent imaging system. On Day Two or Three, the patients can receive 5 mCi (180 MBq) of $^{124}$I on an escalating dose of anti-MISIIR diabody (5, 10, 20, 30 or 40 mg) by i.v. bolus injection. Whole body PET/CT images can be acquired and blood samples also can be obtained at about one hour, 4-8 hours, 24 hours, 48 hours, 72 hours and 120 hours after administration. Regions of interest can be drawn around critical organs and the amount of localized activity can be determined. Blood samples can be counted along with standards in a gamma well counter to determine the activity remaining in circulation. The projected radiation exposure to each organ and to bone marrow that would have been associated with a therapeutic dose if $^{131}$I was used in place of $^{124}$I can then be determined using the MIRD Dose 3 software package (Oak Ridge Associated Universities).

Safety can be determined by the ongoing monitoring of the incidence and intensity of adverse events graded by the Common Toxicity Criteria. Following injection of the radiopharmaceuticals, whole body PET/CT imaging can be performed immediately at the time points indicated above. As the diabody is a novel construct, regular blood samples can be obtained to assay for the development of human anti-diabody antibodies (HADA). These data can be used to obtain dosimetry estimates to determine if $^{131}$I labeled anti-MISIIR diabody would be associated with a predicted therapeutic effect and could be safely administered to patients. If so, this can provide justification for proceeding to a separate radioimmunotherapy clinical trial employing the $^{131}$I labeled anti-MISIIR diabody.

Statistical analysis of the results of this study can be performed as follows. Briefly, logistic regression can be conducted to model the probability of DLT (dose-limiting toxicity) or of efficacious response as a function of protein dose. Polynomial functions of dose can be considered to permit the possibility of non-monotone dependence on dose (e.g., maximal efficacy achieved at a dose strictly less than the maximum administered in the study). The logistic regression models can provide an estimate of the lowest protein dose such that (1) the estimated percentage of patients expected to exhibit favorable dosimetry is at least 50% and (2) the estimated prevalence of DLT is no greater than 10%. Generalized estimating equations in the context of logistic regression can be used to model the probability of a positive diagnosis (i.e., sensitivity) as a function of protein dose and image agent (i.e., compare $^{18}$FDG and multiple $^{124}$I-based images).

EXAMPLE 6

Therapy Studies

The ability of unconjugated diabody to treat ovarian cancer xenografts can be determined. If available, diabodies that either inhibit or do not suppress in vitro tumor cell growth can be employed as controls in these studies. An example of such studies is described briefly here. 8-12 week old SCID mice can receive s.c. implants of 5×10$^6$ OVCAR-3, IGROV-1, or SK-OV-3 ovarian cancer cells. After the tumors have grown to approximately 100 mm$^3$, cohorts of about 10 mice can be treated daily with four escalating dose levels, which can be determined based upon the results of the in vitro studies described hereinabove, of the diabody clone that exhibited the greatest efficacy in the in vitro growth inhibition studies described hereinabove. The mice can be observed for tumor growth and treatment-related toxicity by noting, e.g., weight loss and distress (Adams, G. P., et al. (2000) Nuc. Med. and Biol., 27:339-346). Tumors can be measured (length×width×depth) with calipers about three times per week and the total volume can be calculated using the ellipsoidal method (Hann, H. W. L., et al. (1992) Cancer, 70:2051-2056). If these results indicate that the unconjugated diabody is associated with an in vivo anti-tumor effect, the $V_H$ and $V_L$ domains can be incorporated into a human IgG1 molecule to potentially afford greater bioavailability and the therapeutic potential of the resulting anti-MISIIR IgG can be assessed.

The ability of the anti-MISIIR diabody and IgG to treat early, spontaneously occurring ovarian tumors in the MISIIR-TAg transgenic mouse model can also be assessed. Briefly, the MISIIR-TAg transgenic mouse line expresses the transforming region (TAg) of simian virus 40 (SV40) under the control of the MISIIR promoter (Connolly, D. C., et al. (2003) Cancer Res., 1389-1397). Approximately 50% of the female MISIIR-TAg mice develop ovarian tumors between 6 and 13 weeks of age. These ovarian tumors, in addition to a cell line, MOVCAR, derived from the ascites of the MISIIR-TAg mice, express endogenous MISIIR and TAg as determined by RT-PCR (Connolly, D. C., et al. (2003) Cancer Res., 1389-1397). The ability of the anti-MISIIR diabody and IgG to treat the ovarian tumors in MISIIR-TAg mice can be determined by the following example. Briefly, cohorts of approximately 10 MISIIR-TAg mice can be treated with unconjugated anti-MISIIR diabody or IgG or left untreated at about 6, 9 and 12 weeks of age. The mice can be euthanized and dissected when approximately 30-50% of the untreated control mice display evidence of tumor formation (e.g., ascites). After documenting evidence of gross lesions, the tissues can be fixed in formalin and processed for histopathological examination. The significance of therapy efficacy with unconjugated anti-MISIIR diabody and IgG can be determined by comparing tumor growth in the presence of the agent compared to tumor growth in the controls.

The anti-MISIIR antibodies can also be tested in radioimmunotherapy studies as exemplified herein. Diabody molecules typically display several characteristics such as rapid renal elimination, more efficient tumor penetration and higher binding avidity that frequently make diabodies superior to other antibody formats, such as intact IgG, (scFv)$_2$ and scFv, in radioimmunotherapy. Therefore, the diabody constructs with the best-predicted dosimetry as described hereinabove can be assessed for their ability to serve as a vehicle for the radioimmunotherapy of solid tumors. Notably, diabodies with similar affinities but contrasting impacts on in vitro growth (e.g., one diabody that inhibits growth and one that does not) may be employed to determine if any growth inhibitory signaling is synergistic or additive with radioimmunotherapy. Inasmuch as scid mice have been found to be hypersensitive to ionizing radiation due to defects in DNA repair (Biedermann, K. A., et al. (1991) Proc, Natl, Acad. Sci., 88:1394-1397), therapy trials can be performed in, for example, athymic nude mice.

Initially, the maximum tolerated dose (MTD) and LD$_{10}$ can be determined as follows. The diabody will be labeled at a specific activity approximating 5 mCi (180 MBq) of $^{131}$I per mg diabody. Notably, $^{90}$Y and $^{177}$Lu, among other isotopes, can be used in place of $^{131}$I in radioimmunotherapy, particularly if the radioiodine-labeled diabodies are rapidly internalized. A single i.v. dose, employing one of at least about five different doses, can be given to cohorts of about 5 non-tumor bearing athymic nude mice. The mice can then be observed for signs of toxicity (e.g., weight loss, petechiae, and death) and the maximum tolerated dose can then be identified as that at which all of the treated mice survive with less than about a 10% loss of body weight. The LD$_{10}$ can be defined as the dose associated with 10% mortality. Inasmuch as the biodistribution data for diabodies indicate that the greatest degree of normal organ retention occurs in the kidneys, renal retention may largely define the maximally-tolerated dose (MTD) in clinical radioimmunotherpy trials. Accordingly, the long-term effects of this therapy on the kidneys can also be determined. Briefly, the mice from these toxicity studies can be studied for about one year wherein monthly blood samples can be acquired, for example, by retro-orbital bleeding to evaluate levels of markers that are associated with renal failure (e.g., blood urea nitrogen and serum creatinine). After about one year, the mice can be euthanized and their tissues can be fixed for histopathological examination. Particular scrutiny can be placed upon the evaluation of the kidneys and bone marrow.

Cohorts of approximately ten mice bearing subcutaneous OVCAR-3, IGROV-1, or SK-OV-3 tumors can be treated at the MTD for all schedules of each molecule to be tested. Duplicate experiments can be performed in mice with small (~2 mm$^3$) palpable tumors and a second set of treatment studies can be performed in mice bearing established (~10 mm$^3$) tumors. In all experiments, the radiolabeled diabody can be administered by i.v. bolus injection in a maximum volume of about 200 µL. The therapeutic effects can be monitored by serially measuring tumor size (as described hereinabove) and sacrificing animals whose tumors exceed about 2 cm in greatest diameter and by plotting both tumor growth rates and times to sacrifice. All studies can include one or more of the following: groups that do not receive treatment, groups treated with radiolabeled growth inhibitory diabody, groups treated with radiolabeled non-growth inhibitory diabody with or without the same affinity, and groups treated with unlabeled forms of both diabodies.

As intraperitoneal (i.p.) models are particularly germane to ovarian cancer, the above-described studies can be performed in nude mice at 7 and 14 days following the i.p. injection of 4×10$^6$ OVCAR-3, IGROV-1, or SK-OV-3 cells. In this model, evidence of abdominal distention typically occurs after about 42 days and tumors are routinely observed within the peritoneum, within the intrabursal space and within the ovaries. In these studies, the mice can be followed for survival following the methods previously described in a study of antibody-based therapy of ovarian cancer in a SCID mouse model (Weiner, L. M., et al., (1993) Cancer Res., 53:94-100).

Future studies can examine the combined effect of anti-MISIIR diabodies (growth inhibitory and non-growth inhibitory) with subcurative doses of chemotherapeutic agents that are active in ovarian cancer such as, without limitation, taxanes, platinum, carboplatin, and combinations of two or more agents such as gemcitabine with cisplatin, topotecan, and/or doxorubicin. Additionally, the efficacy of anti-MISIIR diabody-based radioimmunotherapy followed by sub-curative chemotherapy in the mouse model can be examined.

The tumor targeting and dosimetry of anti-MISIIR antibodies in addition to toxicities and MTDs can also be determined in humans. For example, women with metastatic, measurable MISIIR expressing ovarian cancer, as in the human imaging trials described hereinabove, can receive a scout dose consisting of an intravenous injection of 5 mCi (180 MBq) of $^{131}$I on 5 mg of diabody. Whole body images can be acquired on a gamma camera and blood samples can also be taken at about one hour, 4-8 hours, 24 hours, 48 hours, 72 hours and 120 hours after administration. Regions of interest can be drawn around critical organs and the amount of localized activity can be determined. Blood samples can be counted along with standards in a gamma well counter to determine the activity remaining in circulation. The projected radiation exposure to each organ and to bone marrow associated with the patient's planned therapeutic dose can then be determined using the MIRD Dose 3 software package (Oak Ridge Associated Universities). If the exposure is predicted to be within safe limits for all critical organs, the patient can be treated as described below on day 8 using the optimal total diabody protein dose identified in the first trial described above. Cohorts of about 3-6 patients will be treated in a standard dose-escalation schema. Dose escalation are preferably not permitted until at least six weeks have elapsed following treatment of the last patient on a current dose cohort. An example of dose escalation is seen in Table 1.

TABLE 1

| Dose Level | Pts. | Diabody Dose | Radionuclide Dose (mCi) |
|---|---|---|---|
| 1 | 3 | Fixed[a] | 10 mCi[b] |
| 2 | 3 | Fixed | 20 mCi |
| 3 | 3 | Fixed | 40 mCi |
| 4 | 3 | Fixed | 55 mCi |
| 5 | 3 | Fixed | 65 mCi |
| 6 | 3-6 | Fixed | 75 mCi[c] |

[a]The total diabody protein dose can be the optimal dose that was identified in the first trial.
[b]If one dose-limiting toxicity (DLT) is observed in the first three patients at a given dose level, another three patients can be accrued to that dose level. If >2/6 patients exhibit DLT in a given dose cohort, that dose can be considered to exceed the MTD, and an additional 3-6 patients can be treated at the next highest dose level to confirm it does not exceed the MTD.
[c]Dose-escalation in 5 mCi (180 MBq) increments can continue in three-patient cohorts until MTD has been identified. Six weeks must elapse from treatment of the last patient in a dose cohort before dose-escalation can occur.

Safety can be determined by the ongoing monitoring of the incidence and intensity of adverse events graded by, for example, the Common Toxicity Criteria (see, e.g., www.fda.gov/cder/cancer). Following injection of the radiopharmaceutical scout dose, whole body gamma camera imaging, optionally with SPECT (single photon emission computed tomography) capabilities, can be performed immediately after administration at the time points indicated above. The sensitivity and specificity of gamma camera imaging can be determined by comparing SPECT images with CT scans. Therapeutic efficacy can be determined by comparing pre- and post-treatment CT scans of known tumor deposits (CT scans can be acquired every six weeks for the first three months following therapy and then every two months thereafter until there is evidence of progression). As the diabody is a novel construct, regular blood samples can be obtained regularly to assay for the development of human anti-diabody antibodies (HADA). Statistical analysis of the results can be performed as described hereinabove in Example 5. As an example, the therapeutically effective dosage amount for a patient may be 50-200 mCi.

While the above demonstrates the therapeutic use of anti-MISIIR antibody molecules conjugated to radioisotopes, similar studies can be performed for immunotoxins and anti-MISIIR antibody molecules conjugated to chemotherapeutic agents.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated antibody which specifically binds the Mullerian Inhibiting Substance Type II Receptor (MISIIR), wherein said antibody is selected from the group consisting of IgG, Fab, Fab', Fv, and F(ab')$_2$, wherein the amino acid sequence of the VH domain of said antibody comprises amino acids 1-131 of SEQ ID NO: 13, wherein the amino acid sequence of the VL domain of said antibody comprises amino acids 147-266 SEQ ID NO: 13, and wherein said MISIIR is a polypeptide consisting of the amino acid sequence of SEQ ID NO: 19.

2. The antibody of claim 1, wherein said antibody is conjugated to a radioisotope.

3. The antibody of claim 2, wherein said radioisotope is selected from the group consisting of $^{90}$Y, $^{177}$Lu, $^{131}$I, and $^{186}$Re.

4. A composition comprising an antibody of claim 1 and a pharmaceutically acceptable carrier.

5. The antibody of claim 1, wherein said antibody is conjugated to at least one molecule selected from the group consisting of a radioisotope, a detectable label, a toxin, a magnetic bead, a pro-drug, a pro-drug converting enzyme, and a chemotherapeutic agent.

6. The antibody as claimed in claim 5, wherein said molecule is a toxin selected from the group consisting of saprin, ricin, abrin, ethidium bromide, diptheria toxin, Pseudomonas exotoxin, PE40, PE38, saporin, gelonin, RNAse, protein nucleic acids (PNAs), ribosome inactivating protein (RIP), type-1 or type-2, pokeweed anti-viral protein (PAP), bryodin, momordin, and bouganin.

7. A method for detecting the presence of MISIIR in a biological sample comprising:
   a) providing a biological sample;
   b) incubating said sample in the presence and absence of the antibody of claim 1, said antibody being detectably labeled; and
   c) determining the presence of said MISIIR as a function of the amount of detectable label bound to said sample.

8. The method of claim 7, further comprising contacting the sample with a non-specific antibody as a negative control.

9. The method of claim 7, wherein said biological sample is selected from the group consisting of blood, plasma, urine, tumor cells, blood cells, ovarian cells, prostate cells, breast cells, testicular cells, cervical cells, lung cells, and nipple aspirates.

10. The antibody of claim 1, wherein said antibody is an IgG.

* * * * *

SEQUENCE LISTING

<160> NUMBER OF SEQ ID NOS: 19

<210> SEQ ID NO 1
<211> LENGTH: 767
<212> TYPE: DNA
<213> ORGANISM: Artificial Sequence
<220> FEATURE:
<223> OTHER INFORMATION: Synthetic Sequence

<400> SEQUENCE: 1
atggcccagg tcaccttgaa ggagtctggt cctacgctgg tgaaacccac acagaccctc    60

| | |
|---|---|
| acgctgacct gcacgttctc tgggttctca ctcaccacta gtggagtggg tgtgggctgg | 120 |
| atccgtcagg ccccaggaaa ggccccggag tggcttgcac tcattgattg ggatgacgat | 180 |
| aaatactaca gcacatctct gaagaccagg ctcaccatct ccaaggacac ctccaaaaac | 240 |
| caggtggtcc ttacaatgac caacatggac cctgtggaca cagccacata ttactgtgcc | 300 |
| cgggactctt attatggctc ggggagtcat tttgacttct ggggccaggg aaccctggtc | 360 |
| accgtctcct caggtggcgg cggttccgga ggtggtggtt ctggcggtgg tggcagctcc | 420 |
| tatgagctga ctcagccacc ctcagtgtcc gtgtccctg acagacagc caccatcacc | 480 |
| tgttctggac atgacttgcg gaataaatat gctcattggt atcagcagaa gccaggacag | 540 |
| tcccctgtgc tggtcgtcta tcaagatgct aagcggccct caggaatccc tgagcgattc | 600 |
| tctggctcca actctgggaa cacagccact ctgaccatca gcgggaccca ggctatggat | 660 |
| gaggctgact attactgtca gacgtgggac aggagcacag tggtcttcgg cggagggacc | 720 |
| aagctgaccg tcctaggtca gcccaaggct gccccctcgg cggccgc | 767 |

<210> SEQ ID NO 2
<211> LENGTH: 800
<212> TYPE: DNA
<213> ORGANISM: Artificial Sequence
<220> FEATURE:
<223> OTHER INFORMATION: Synthetic Sequence

<400> SEQUENCE: 2

| | |
|---|---|
| atggcccagg tgcagctggt gcagtctgga actgaggtga agaggcctgg ggcctcagtg | 60 |
| aagatctcct gcagggctac tggttacacc tttagtgatt atggtatcag ttggatgcga | 120 |
| caggcccctg gacaagggct tgagtggatg ggatggatca gcgcttacaa tggtaacaca | 180 |
| aactatgcac agaagctcca gggcagagtc accatgacca cagacacgtc cacgagcaca | 240 |
| gcctacatgg agctgaggag cctcagatat gacgacacgg ccgtatatta ctgtgcgaga | 300 |
| gatgggaggc gtggttcggg tatttactgg ggtgtgtatt attacaacgg tatggacgtc | 360 |
| tggggccaag gaccacggt caccgtctcc tcaggtggcg gcggttccgg aggtggtggt | 420 |
| tctggcggtg gtggcagtca gcctgtgctg actcagccac cctcagcgtc tgggaccccc | 480 |
| gggcagaggg tcaccatctc ttgttctgga agcaggtcca acatcggaag gaataccgta | 540 |
| aactggtatc agcaggtccc aggaatggcc cccaaactcc tcatctatag taataatcag | 600 |
| cggccctcag gggtccctga ccgattctct ggctccaagt ctggcacctc agcctccctg | 660 |
| gccatcagtg ggctccagtc tgaggatgag gctgattatt actgtgcagc atgggatgac | 720 |
| agtctgaatg gtgtggtatt cggcggaggg accaagctga ccgtcctagg tcagcccaag | 780 |
| gccgcccct cggcggccgc | 800 |

<210> SEQ ID NO 3
<211> LENGTH: 782
<212> TYPE: DNA
<213> ORGANISM: Artificial Sequence
<220> FEATURE:
<223> OTHER INFORMATION: Synthetic Sequence

<400> SEQUENCE: 3

| | |
|---|---|
| atggcccagg tgcagctggt gcagtctgga ggaggcttgg tccagcctgg ggggtccctg | 60 |
| agactctcct gtgcagcctc tgggttcacc gtcagtagca actacatgag ctgggtccgc | 120 |
| caggctccag ggaaggggct ggagtgggtc tcagctatta gtggtagtgg tggtagcaca | 180 |
| tactacgcag actccgtgaa gggccggttc accatctcca gagacaattc caagaacacg | 240 |

| | |
|---|---|
| ctgtatctgc aaatgaacag cctgagagcc gaggacacgg ccgtatatta ctgtgcgacg | 300 |
| cgcccttcaa ggggtagcag tggctggtac ggggggggact actggggcca gggaaccctg | 360 |
| gtcaccgtct cctcaggtgg cggcggttcc ggaggtggtg gttctggcgg tggtggcagc | 420 |
| tcctatgagc tgactcagcc accctcaact tctgggactc ccgggcagag ggtcaccatc | 480 |
| tcttgttctg gaagcacctc caacatcgca actaataatg taaactggta ccagttcctc | 540 |
| ccaggaacgg cccccaaact cctcatgtat cggaatgatc agcggcccgc aggggtccct | 600 |
| gaccgattct ctggctccaa gtctggcacc tcagcctccc tggccatcag tgggctccaa | 660 |
| cctgaggatg aggctgacta ttactgtgca gcatgggatg acagcctggg tggcgaggtc | 720 |
| ttcggaactg ggaccaaggt caacgtccta ggtcagccca aggccgcccc ctcggcggcc | 780 |
| gc | 782 |

<210> SEQ ID NO 4
<211> LENGTH: 789
<212> TYPE: DNA
<213> ORGANISM: Artificial Sequence
<220> FEATURE:
<223> OTHER INFORMATION: Synthetic Sequence

<400> SEQUENCE: 4

| | |
|---|---|
| atggcccagg tgcagctggt gcagtctgga actgaggtga agaggcctgg ggcctcagtg | 60 |
| aagatctcct gcagggctac tggttacacc tttagtgatt atggtatcag ttggatgcga | 120 |
| caggcccctg gacaagggct tgagtggatg ggatggatca cgcttacaa tggtaacaca | 180 |
| aactatgcac agaagctcca gggcagagtc accatgacca cagacacgtc cacgagcaca | 240 |
| gcctacatgg agctgaggag cctcagatat gacgacacgg ccgtatatta ctgtgcgaga | 300 |
| gatgggaggc gtggttcggg tatttactgg ggtgtgtatt attacaacgg tatggacgtc | 360 |
| tggggccaag gaccacggt caccgtctcc tcaggtggcg cggttccgg aggtggtggt | 420 |
| tctggcggtg gtggcagtca gcctgtgctg actcagccac cctcagcgtc tgggaccccc | 480 |
| gggcagaggg tcaccatctc ttgttctgga agcaggtcca acatcggaag gaataccgta | 540 |
| aactggtatc agcaggtccc aggaatggcc ccaaactcc tcatctatag taataatcag | 600 |
| cggccctcag gggtccctga ccgattctct ggctccaagt ctggcacctc agcctccctg | 660 |
| gccatcagtg ggctccagtc tgaggatgag gctgattatt actgtgcagc atgggatgac | 720 |
| agtctgaatg gtgtggtatt cggcggaggg accaagctga ccgtcctagg tcagcccaag | 780 |
| gccgccccc | 789 |

<210> SEQ ID NO 5
<211> LENGTH: 798
<212> TYPE: DNA
<213> ORGANISM: Artificial Sequence
<220> FEATURE:
<223> OTHER INFORMATION: Synthetic Sequence

<400> SEQUENCE: 5

| | |
|---|---|
| atggcccaga tcaccttgaa ggagtctggt cctacgctgg tgaaacccac acagaccctc | 60 |
| acgctgacct gcaccgtctc tgggttctca ctcagcaatg ctagaatggg tgtgagctgg | 120 |
| atccgtcagc cccaggaaaa ggccctggag tggcttgcac tcatttatcg ggataatgat | 180 |
| aagcgctaca acccatctct gaagagcagg ctcaccatca ccaaggacac ctcgaaaaac | 240 |
| caagtggtcc tgacaatgag caacatggac cctgtgacac agccacata ttactgtgca | 300 |
| cacagcctcg tagtaccagc tgctaatccc tttgactact ggggccaggg aaccctggtc | 360 |

| | |
|---|---|
| accgtctcct catcggcctc gggggccgaa ttgggcggcg gcggctccgg aggaggagga | 420 |
| tctggtggtg gtggttcgac tagtcaggct gtgctgactc agccgtcttc cctctctgca | 480 |
| tctcctggag catcagccag tctcacctgc accttgcgca gtggcatcaa tgttggtacc | 540 |
| tacaggatat actggtacca gcagaagcca gggagtcctc cccagtatct cctgaggtac | 600 |
| aaatcagact cagataagca aagggctct ggagtcccca gccgcttctc tggatccaaa | 660 |
| gatgcttcgg ccaatgcagg gatttactc atctctgggc tccagtctga ggatgaggct | 720 |
| gactattatt gtatgatttg gcacaccagc gcttatgtct tcggaactgg gaccaaggtc | 780 |
| accgtcctag gctcgagc | 798 |

<210> SEQ ID NO 6
<211> LENGTH: 771
<212> TYPE: DNA
<213> ORGANISM: Artificial Sequence
<220> FEATURE:
<223> OTHER INFORMATION: Synthetic Sequence
<220> FEATURE:
<221> NAME/KEY: unsure
<222> LOCATION: (15)...(15)
<223> OTHER INFORMATION: n = a, g, c or t

<400> SEQUENCE: 6

| | |
|---|---|
| atggccgagg tgcanctggt gcagtctggg ggaggcgtgg tccagcctgg gaggtccctg | 60 |
| agactctcct gtgacgcctc tggattcgtc ttcagtaatt atgctgtcca ctgggtccgc | 120 |
| caggctccag gcaaggggct agaatgggtg gcagctattt cacctgatgg gaggtatata | 180 |
| cattatggag actccgtgca gggccgattc accgtgtcca gagacaacgc cagagcacc | 240 |
| ctgtatctgc aaatgaacag tctgagagcc gaggacacgg ctgtctatta ttgtgcaaga | 300 |
| gatcgaggga ggcctgatgc tttcgatatc tggggccaag gacaatggt caccgtctct | 360 |
| tcaggtggcg gcggttccgg aggtggtggt tctggcggtg gtggcagcca gtctgtgctg | 420 |
| actcagccac cctccgcgtc cgggtctcct ggacagtcag tcaccatctc ctgcaccgga | 480 |
| accagcagtg acgttggcgc ttatgaccat gtctcttggt accaacaaca cccagacaaa | 540 |
| gcccccaaac tcatcattta tgaggtcaat agacggccct caggggtccc tgatcgcttc | 600 |
| tctggctcca gtctggcaa cacggcctcc ctgaccgtct ctggcctcca gattgaggat | 660 |
| gaggctgatt acttctgcac ctcatattca cgaattaacg attatgtctt cggacctggg | 720 |
| accagggtcg ccgtcctcgg tcagcccaag gctaccccct cggcggccgc a | 771 |

<210> SEQ ID NO 7
<211> LENGTH: 771
<212> TYPE: DNA
<213> ORGANISM: Artificial Sequence
<220> FEATURE:
<223> OTHER INFORMATION: Synthetic Sequence

<400> SEQUENCE: 7

| | |
|---|---|
| atggctcagg tgcagctggt gcagtctggg gctgaggtga agaagcctgg ggcctcagtg | 60 |
| aaggtctcct gcaaggcttc tggatacacc ttcaccagtt atgatatcaa ctgggtgcga | 120 |
| caggccactg gacaagggct tgagtggatg ggatggatga acctaacag tggtaacaca | 180 |
| ggctatgcac agaagttcca gggcagagtc accatgacca gaacacctc cactaataca | 240 |
| gcctacatgg aactgaccag cctgacatct gaggacacgg ccgtgtatta ctgtgcgaga | 300 |
| ggcagcccat ccccgatgaa cgtctgggc caagggacca cggtcaccgt ctcctcaggt | 360 |
| ggcggcggtt ccggaggtgg tggttctggc ggtggtggca gccagcctgt gctgactcag | 420 |

| | | |
|---|---|---|
| ccccactctg tgtcggagtc tccggggaag acggtaacca tctcctgcac ccgcagcagt | 480 | |
| gggagcattg ccaacgacta tgttcagtgg ttccagcagc gcccgggcag tgccccacc | 540 | |
| attgtgatct atgaagatta ccgaagaccc tctggggtcc ctgatcggtt ctctggctcc | 600 | |
| atcgacagct cctccaactc tgcctccctc accatctctg gactgaagac tgaggacgag | 660 | |
| gctgactact actgtcagtc ttatgatagc agcaatcctt atgtggtatt cggcggaggg | 720 | |
| accaagctga ccgtcctagg tcagcccaag gctgccccct cggcggccgc a | 771 | |

<210> SEQ ID NO 8
<211> LENGTH: 1118
<212> TYPE: DNA
<213> ORGANISM: Artificial Sequence
<220> FEATURE:
<223> OTHER INFORMATION: Synthetic Sequence

<400> SEQUENCE: 8

| | | |
|---|---|---|
| ggcgcgccca ccatcaccat caccatcccc caaacaggcg aacctgtgtg ttctttgagg | 60 | |
| cccctggagt gcggggaagc acaaagacac tgggagagct gctagataca ggcacagagc | 120 | |
| tccccagagc tatccgctgc ctctacagcc gctgctgctt tgggatctgg aacctgaccc | 180 | |
| aagaccgggc acaggtggaa atgcaaggat gccgagacag tgatgagcca ggctgtgagt | 240 | |
| ccctccactg tgacccaagt ccccgagccc accccagccc tggctccact ctcttcacct | 300 | |
| gctcctgtgg cactgacttc tgcaatgcca attacagcca tctgcctcct cagggagcc | 360 | |
| ctgggactcc tggctcccag gtccccagg ctgccccagg tgagtccggt accgttgagc | 420 | |
| ccaaatcttg tgacaaaact cacacatgcc caccgtgccc agcacctgaa ctcctggggg | 480 | |
| gaccgtcagt cttcctcttc cccccaaaac ccaaggacac cctcatgatc tcccggaccc | 540 | |
| ctgaggtcac atgcgtggtg gtggacgtga gccacgaaga ccctgaggtc aagttcaact | 600 | |
| ggtacgtgga cggcgtggag gtgcataatg ccaagacaaa gccgcgggag gagcagtaca | 660 | |
| acagcacgta ccgtgtggtc agcgtcctca ccgtcctgca ccaggactgg ctgaatggca | 720 | |
| aggagtacaa gtgcaaggtc tccaacaaag ccctcccagc cccatcgag aaaaccatct | 780 | |
| ccaaagccaa agggcagccc cgagaaccac aggtgtacac cctgccccca tcccgggatg | 840 | |
| agctgaccaa gaaccaggtc agcctgacct gcctggtcaa aggcttctat cccagcgaca | 900 | |
| tcgccgtgga gtgggagagc aatgggcagc cggagaacaa ctacaagacc acgcctcccg | 960 | |
| tgctggactc cgacggctcc ttcttcctct acagcaagct caccgtggac aagagcaggt | 1020 | |
| ggcagcaggg gaacgtcttc tcatgctccg tgatgcatga ggctctgcac aaccactaca | 1080 | |
| cgcagaagag cctctccctg tctccgggta aactcgag | 1118 | |

<210> SEQ ID NO 9
<211> LENGTH: 255
<212> TYPE: PRT
<213> ORGANISM: Artificial Sequence
<220> FEATURE:
<223> OTHER INFORMATION: Synthetic Sequence

<400> SEQUENCE: 9

```
Met Ala Gln Val Thr Leu Lys Glu Ser Gly Pro Thr Leu Val Lys Pro
1               5                   10                  15

Thr Gln Thr Leu Thr Leu Thr Cys Thr Phe Ser Gly Phe Ser Leu Thr
            20                  25                  30

Thr Ser Gly Val Gly Val Gly Trp Ile Arg Gln Ala Pro Gly Lys Ala
        35                  40                  45
```

```
Pro Glu Trp Leu Ala Leu Ile Asp Trp Asp Asp Lys Tyr Tyr Ser
    50                  55                  60

Thr Ser Leu Lys Thr Arg Leu Thr Ile Ser Lys Asp Thr Ser Lys Asn
65                  70                  75                  80

Gln Val Val Leu Thr Met Thr Asn Met Asp Pro Val Asp Thr Ala Thr
                    85                  90                  95

Tyr Tyr Cys Ala Arg Asp Ser Tyr Tyr Gly Ser Gly Ser His Phe Asp
                100                 105                 110

Phe Trp Gly Gln Gly Thr Leu Val Thr Val Ser Ser Gly Gly Gly Gly
            115                 120                 125

Ser Gly Gly Gly Gly Ser Gly Gly Gly Ser Ser Tyr Glu Leu Thr
130                 135                 140

Gln Pro Pro Ser Val Ser Val Ser Pro Gly Gln Thr Ala Thr Ile Thr
145                 150                 155                 160

Cys Ser Gly His Asp Leu Arg Asn Lys Tyr Ala His Trp Tyr Gln Gln
                165                 170                 175

Lys Pro Gly Gln Ser Pro Val Leu Val Val Tyr Gln Asp Ala Lys Arg
            180                 185                 190

Pro Ser Gly Ile Pro Glu Arg Phe Ser Gly Ser Asn Ser Gly Asn Thr
            195                 200                 205

Ala Thr Leu Thr Ile Ser Gly Thr Gln Ala Met Asp Glu Ala Asp Tyr
210                 215                 220

Tyr Cys Gln Thr Trp Asp Arg Ser Thr Val Val Phe Gly Gly Gly Thr
225                 230                 235                 240

Lys Leu Thr Val Leu Gly Gln Pro Lys Ala Ala Pro Ser Ala Ala
            245                 250                 255

<210> SEQ ID NO 10
<211> LENGTH: 266
<212> TYPE: PRT
<213> ORGANISM: Artificial Sequence
<220> FEATURE:
<223> OTHER INFORMATION: Synthetic Sequence

<400> SEQUENCE: 10

Met Ala Gln Val Gln Leu Val Gln Ser Gly Thr Glu Val Lys Arg Pro
1               5                   10                  15

Gly Ala Ser Val Lys Ile Ser Cys Arg Ala Thr Gly Tyr Thr Phe Ser
                20                  25                  30

Asp Tyr Gly Ile Ser Trp Met Arg Gln Ala Pro Gly Gln Gly Leu Glu
            35                  40                  45

Trp Met Gly Trp Ile Ser Ala Tyr Asn Gly Asn Thr Asn Tyr Ala Gln
    50                  55                  60

Lys Leu Gln Gly Arg Val Thr Met Thr Thr Asp Thr Ser Thr Ser Thr
65                  70                  75                  80

Ala Tyr Met Glu Leu Arg Ser Leu Arg Tyr Asp Asp Thr Ala Val Tyr
                85                  90                  95

Tyr Cys Ala Arg Asp Gly Arg Arg Gly Ser Gly Ile Tyr Trp Gly Val
                100                 105                 110

Tyr Tyr Tyr Asn Gly Met Asp Val Trp Gly Gln Gly Thr Thr Val Thr
            115                 120                 125

Val Ser Ser Gly Gly Gly Gly Ser Gly Gly Gly Gly Ser Gly Gly Gly
130                 135                 140

Gly Ser Gln Pro Val Leu Thr Gln Pro Pro Ser Ala Ser Gly Thr Pro
145                 150                 155                 160

Gly Gln Arg Val Thr Ile Ser Cys Ser Gly Ser Arg Ser Asn Ile Gly
```

```
                165                 170                 175
Arg Asn Thr Val Asn Trp Tyr Gln Gln Val Pro Gly Met Ala Pro Lys
            180                 185                 190

Leu Leu Ile Tyr Ser Asn Asn Gln Arg Pro Ser Gly Val Pro Asp Arg
            195                 200                 205

Phe Ser Gly Ser Lys Ser Gly Thr Ser Ala Ser Leu Ala Ile Ser Gly
            210                 215                 220

Leu Gln Ser Glu Asp Glu Ala Asp Tyr Tyr Cys Ala Ala Trp Asp Asp
225                 230                 235                 240

Ser Leu Asn Gly Val Val Phe Gly Gly Gly Thr Lys Leu Thr Val Leu
                245                 250                 255

Gly Gln Pro Lys Ala Ala Pro Ser Ala Ala
            260                 265

<210> SEQ ID NO 11
<211> LENGTH: 260
<212> TYPE: PRT
<213> ORGANISM: Artificial Sequence
<220> FEATURE:
<223> OTHER INFORMATION: Synthetic Sequence

<400> SEQUENCE: 11

Met Ala Gln Val Gln Leu Val Gln Ser Gly Gly Gly Leu Val Gln Pro
1               5                   10                  15

Gly Gly Ser Leu Arg Leu Ser Cys Ala Ala Ser Gly Phe Thr Val Ser
            20                  25                  30

Ser Asn Tyr Met Ser Trp Val Arg Gln Ala Pro Gly Lys Gly Leu Glu
        35                  40                  45

Trp Val Ser Ala Ile Ser Gly Ser Gly Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Thr Arg Pro Ser Arg Gly Ser Ser Gly Tyr Gly Gly
            100                 105                 110

Asp Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Ser Tyr Glu Leu
    130                 135                 140

Thr Gln Pro Pro Ser Thr Ser Gly Thr Pro Gly Gln Arg Val Thr Ile
145                 150                 155                 160

Ser Cys Ser Gly Ser Thr Ser Asn Ile Ala Thr Asn Asn Val Asn Trp
                165                 170                 175

Tyr Gln Phe Leu Pro Gly Thr Ala Pro Lys Leu Leu Met Tyr Arg Asn
            180                 185                 190

Asp Gln Arg Pro Ala Gly Val Pro Asp Arg Phe Ser Gly Ser Lys Ser
        195                 200                 205

Gly Thr Ser Ala Ser Leu Ala Ile Ser Gly Leu Gln Pro Glu Asp Glu
    210                 215                 220

Ala Asp Tyr Tyr Cys Ala Ala Trp Asp Ser Leu Gly Gly Glu Val
225                 230                 235                 240

Phe Gly Thr Gly Thr Lys Val Asn Val Leu Gly Gln Pro Lys Ala Ala
                245                 250                 255

Pro Ser Ala Ala
        260
```

<210> SEQ ID NO 12
<211> LENGTH: 263
<212> TYPE: PRT
<213> ORGANISM: Artificial Sequence
<220> FEATURE:
<223> OTHER INFORMATION: Synthetic Sequence

<400> SEQUENCE: 12

```
Met Ala Gln Val Gln Leu Val Gln Ser Gly Thr Glu Val Lys Arg Pro
 1               5                  10                  15

Gly Ala Ser Val Lys Ile Ser Cys Arg Ala Thr Gly Tyr Thr Phe Ser
            20                  25                  30

Asp Tyr Gly Ile Ser Trp Met Arg Gln Ala Pro Gly Gln Gly Leu Glu
        35                  40                  45

Trp Met Gly Trp Ile Ser Ala Tyr Asn Gly Asn Thr Asn Tyr Ala Gln
    50                  55                  60

Lys Leu Gln Gly Arg Val Thr Met Thr Thr Asp Thr Ser Thr Ser Thr
65                  70                  75                  80

Ala Tyr Met Glu Leu Arg Ser Leu Arg Tyr Asp Asp Thr Ala Val Tyr
                85                  90                  95

Tyr Cys Ala Arg Asp Gly Arg Arg Gly Ser Gly Ile Tyr Trp Gly Val
            100                 105                 110

Tyr Tyr Tyr Asn Gly Met Asp Val Trp Gly Gln Gly Thr Thr Val Thr
        115                 120                 125

Val Ser Ser Gly Gly Gly Gly Ser Gly Gly Gly Gly Ser Gly Gly Gly
    130                 135                 140

Gly Ser Gln Pro Val Leu Thr Gln Pro Pro Ser Ala Ser Gly Thr Pro
145                 150                 155                 160

Gly Gln Arg Val Thr Ile Ser Cys Ser Gly Ser Arg Ser Asn Ile Gly
                165                 170                 175

Arg Asn Thr Val Asn Trp Tyr Gln Gln Val Pro Gly Met Ala Pro Lys
            180                 185                 190

Leu Leu Ile Tyr Ser Asn Asn Gln Arg Pro Ser Gly Val Pro Asp Arg
        195                 200                 205

Phe Ser Gly Ser Lys Ser Gly Thr Ser Ala Ser Leu Ala Ile Ser Gly
    210                 215                 220

Leu Gln Ser Glu Asp Glu Ala Asp Tyr Tyr Cys Ala Ala Trp Asp Asp
225                 230                 235                 240

Ser Leu Asn Gly Val Val Phe Gly Gly Gly Thr Lys Leu Thr Val Leu
                245                 250                 255

Gly Gln Pro Lys Ala Ala Pro
            260
```

<210> SEQ ID NO 13
<211> LENGTH: 266
<212> TYPE: PRT
<213> ORGANISM: Artificial Sequence
<220> FEATURE:
<223> OTHER INFORMATION: Synthetic Sequence

<400> SEQUENCE: 13

```
Met Ala Gln Ile Thr Leu Lys Glu Ser Gly Pro Thr Leu Val Lys Pro
 1               5                  10                  15

Thr Gln Thr Leu Thr Leu Thr Cys Thr Val Ser Gly Phe Ser Leu Ser
            20                  25                  30

Asn Ala Arg Met Gly Val Ser Trp Ile Arg Gln Pro Pro Gly Lys Ala
        35                  40                  45
```

Leu Glu Trp Leu Ala Leu Ile Tyr Arg Asp Asn Asp Lys Arg Tyr Asn
            50                  55                  60

Pro Ser Leu Lys Ser Arg Leu Thr Ile Thr Lys Asp Thr Ser Lys Asn
 65                  70                  75                  80

Gln Val Val Leu Thr Met Ser Asn Met Asp Pro Val Asp Thr Ala Thr
                        85                  90                  95

Tyr Tyr Cys Ala His Ser Leu Val Val Pro Ala Ala Asn Pro Phe Asp
                100                 105                 110

Tyr Trp Gly Gln Gly Thr Leu Val Thr Val Ser Ser Ala Ser Gly
                115                 120                 125

Ala Glu Leu Gly Gly Gly Ser Gly Gly Gly Ser Gly Gly
        130                 135                 140

Gly Ser Thr Ser Gln Ala Val Leu Thr Gln Pro Ser Ser Leu Ser Ala
145                 150                 155                 160

Ser Pro Gly Ala Ser Ala Ser Leu Thr Cys Thr Leu Arg Ser Gly Ile
                165                 170                 175

Asn Val Gly Thr Tyr Arg Ile Tyr Trp Tyr Gln Gln Lys Pro Gly Ser
                180                 185                 190

Pro Pro Gln Tyr Leu Leu Arg Tyr Lys Ser Asp Ser Asp Lys Gln Lys
                195                 200                 205

Gly Ser Gly Val Pro Ser Arg Phe Ser Gly Ser Lys Asp Ala Ser Ala
210                 215                 220

Asn Ala Gly Ile Leu Leu Ile Ser Gly Leu Gln Ser Glu Asp Glu Ala
225                 230                 235                 240

Asp Tyr Tyr Cys Met Ile Trp His Thr Ser Ala Tyr Val Phe Gly Thr
                245                 250                 255

Gly Thr Lys Val Thr Val Leu Gly Ser Ser
                260                 265

<210> SEQ ID NO 14
<211> LENGTH: 257
<212> TYPE: PRT
<213> ORGANISM: Artificial Sequence
<220> FEATURE:
<223> OTHER INFORMATION: Synthetic Sequence
<220> FEATURE:
<221> NAME/KEY: UNSURE
<222> LOCATION: (5)...(5)
<223> OTHER INFORMATION: Xaa = unknown

<400> SEQUENCE: 14

Met Ala Glu Val Xaa Leu Val Gln Ser Gly Gly Gly Val Val Gln Pro
 1               5                  10                  15

Gly Arg Ser Leu Arg Leu Ser Cys Asp Ala Ser Gly Phe Val Phe Ser
                20                  25                  30

Asn Tyr Ala Val His Trp Val Arg Gln Ala Pro Gly Lys Gly Leu Glu
            35                  40                  45

Trp Val Ala Ala Ile Ser Pro Asp Gly Arg Tyr Ile His Tyr Gly Asp
 50                  55                  60

Ser Val Gln Gly Arg Phe Thr Val Ser Arg Asp Asn Ala Gln Ser Thr
 65                  70                  75                  80

Leu Tyr Leu Gln Met Asn Ser Leu Arg Ala Glu Asp Thr Ala Val Tyr
                85                  90                  95

Tyr Cys Ala Arg Asp Arg Gly Arg Pro Asp Ala Phe Asp Ile Trp Gly
                100                 105                 110

Gln Gly Thr Met Val Thr Val Ser Ser Gly Gly Gly Gly Ser Gly Gly
            115                 120                 125

```
Gly Gly Ser Gly Gly Gly Ser Gln Ser Val Leu Thr Gln Pro Pro
        130                 135                 140
Ser Ala Ser Gly Ser Pro Gly Gln Ser Val Thr Ile Ser Cys Thr Gly
145                 150                 155                 160
Thr Ser Ser Asp Val Gly Ala Tyr Asp His Val Ser Trp Tyr Gln Gln
                165                 170                 175
His Pro Asp Lys Ala Pro Lys Leu Ile Ile Tyr Glu Val Asn Arg Arg
            180                 185                 190
Pro Ser Gly Val Pro Asp Arg Phe Ser Gly Ser Lys Ser Gly Asn Thr
        195                 200                 205
Ala Ser Leu Thr Val Ser Gly Leu Gln Ile Glu Asp Glu Ala Asp Tyr
    210                 215                 220
Phe Cys Thr Ser Tyr Ser Arg Ile Asn Asp Tyr Val Phe Gly Pro Gly
225                 230                 235                 240
Thr Arg Val Ala Val Leu Gly Gln Pro Lys Ala Thr Pro Ser Ala Ala
                245                 250                 255
Ala

<210> SEQ ID NO 15
<211> LENGTH: 257
<212> TYPE: PRT
<213> ORGANISM: Artificial Sequence
<220> FEATURE:
<223> OTHER INFORMATION: Synthetic Sequence

<400> SEQUENCE: 15

Met Ala Gln Val Gln Leu Val Gln Ser Gly Ala Glu Val Lys Lys Pro
1               5                   10                  15
Gly Ala Ser Val Lys Val Ser Cys Lys Ala Ser Gly Tyr Thr Phe Thr
                20                  25                  30
Ser Tyr Asp Ile Asn Trp Val Arg Gln Ala Thr Gly Gln Gly Leu Glu
            35                  40                  45
Trp Met Gly Trp Met Asn Pro Asn Ser Gly Asn Thr Gly Tyr Ala Gln
        50                  55                  60
Lys Phe Gln Gly Arg Val Thr Met Thr Arg Asn Thr Ser Thr Asn Thr
65                  70                  75                  80
Ala Tyr Met Glu Leu Thr Ser Leu Thr Ser Glu Asp Thr Ala Val Tyr
                85                  90                  95
Tyr Cys Ala Arg Gly Ser Pro Ser Pro Met Asn Val Trp Gly Gln Gly
                100                 105                 110
Thr Thr Val Thr Val Ser Ser Gly Gly Gly Ser Gly Gly Gly Gly
            115                 120                 125
Ser Gly Gly Gly Gly Ser Gln Pro Val Leu Thr Gln Pro His Ser Val
        130                 135                 140
Ser Glu Ser Pro Gly Lys Thr Val Thr Ile Ser Cys Thr Arg Ser Ser
145                 150                 155                 160
Gly Ser Ile Ala Asn Asp Tyr Val Gln Trp Phe Gln Gln Arg Pro Gly
                165                 170                 175
Ser Ala Pro Thr Ile Val Ile Tyr Glu Asp Tyr Arg Arg Pro Ser Gly
            180                 185                 190
Val Pro Asp Arg Phe Ser Gly Ser Ile Asp Ser Ser Asn Ser Ala
        195                 200                 205
Ser Leu Thr Ile Ser Gly Leu Lys Thr Glu Asp Glu Ala Asp Tyr Tyr
    210                 215                 220
Cys Gln Ser Tyr Asp Ser Ser Asn Pro Tyr Val Val Phe Gly Gly Gly
```

```
                    225                 230                 235                 240
Thr Lys Leu Thr Val Leu Gly Gln Pro Lys Ala Ala Pro Ser Ala Ala
                245                 250                 255
Ala

<210> SEQ ID NO 16
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 16

Gly Thr Glu Leu Pro Arg Ala Ile Arg Cys Leu Tyr Ser Arg
 1               5                  10

<210> SEQ ID NO 17
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 17

Cys Asp Pro Ser Pro Arg Ala His Pro Ser Pro Gly Ser Thr Leu Phe
 1               5                  10                  15

Thr Cys

<210> SEQ ID NO 18
<211> LENGTH: 21
<212> TYPE: PRT
<213> ORGANISM: Artificial Sequence
<220> FEATURE:
<223> OTHER INFORMATION: Synthetic Sequence

<400> SEQUENCE: 18

Asp Ser Asp Glu Pro Gly Cys Glu Ser Leu His Cys Asp Pro Ser Pro
 1               5                  10                  15

Arg Ala His Pro Ser
                20

<210> SEQ ID NO 19
<211> LENGTH: 573
<212> TYPE: PRT
<213> ORGANISM: Homo sapiens

<400> SEQUENCE: 19

Met Leu Gly Ser Leu Gly Leu Trp Ala Leu Leu Pro Thr Ala Val Glu
 1               5                  10                  15

Ala Pro Pro Asn Arg Arg Thr Cys Val Phe Phe Glu Ala Pro Gly Val
                20                  25                  30

Arg Gly Ser Thr Lys Thr Leu Gly Glu Leu Leu Asp Thr Gly Thr Glu
            35                  40                  45

Leu Pro Arg Ala Ile Arg Cys Leu Tyr Ser Arg Cys Cys Phe Gly Ile
        50                  55                  60

Trp Asn Leu Thr Gln Asp Arg Ala Gln Val Glu Met Gln Gly Cys Arg
 65                  70                  75                  80

Asp Ser Asp Glu Pro Gly Cys Glu Ser Leu His Cys Asp Pro Ser Pro
                85                  90                  95

Arg Ala His Pro Ser Pro Gly Ser Thr Leu Phe Thr Cys Ser Cys Gly
            100                 105                 110
```

-continued

```
Thr Asp Phe Cys Asn Ala Asn Tyr Ser His Leu Pro Pro Gly Ser
        115                 120                 125

Pro Gly Thr Pro Gly Ser Gln Gly Pro Gln Ala Ala Pro Gly Glu Ser
    130                 135                 140

Ile Trp Met Ala Leu Val Leu Leu Gly Leu Phe Leu Leu Leu Leu Leu
145                 150                 155                 160

Leu Leu Gly Ser Ile Ile Leu Ala Leu Leu Gln Arg Lys Asn Tyr Arg
                165                 170                 175

Val Arg Gly Glu Pro Val Pro Glu Pro Arg Pro Asp Ser Gly Arg Asp
            180                 185                 190

Trp Ser Val Glu Leu Gln Glu Leu Pro Glu Leu Cys Phe Ser Gln Val
        195                 200                 205

Ile Arg Glu Gly Gly His Ala Val Val Trp Ala Gly Gln Leu Gln Gly
    210                 215                 220

Lys Leu Val Ala Ile Lys Ala Phe Pro Pro Arg Ser Val Ala Gln Phe
225                 230                 235                 240

Gln Ala Glu Arg Ala Leu Tyr Glu Leu Pro Gly Leu Gln His Asp His
                245                 250                 255

Ile Val Arg Phe Ile Thr Ala Ser Arg Gly Gly Pro Gly Arg Leu Leu
            260                 265                 270

Ser Gly Pro Leu Leu Val Leu Glu Leu His Pro Lys Gly Ser Leu Cys
        275                 280                 285

His Tyr Leu Thr Gln Tyr Thr Ser Asp Trp Gly Ser Ser Leu Arg Met
    290                 295                 300

Ala Leu Ser Leu Ala Gln Gly Leu Ala Phe Leu His Glu Glu Arg Trp
305                 310                 315                 320

Gln Asn Gly Gln Tyr Lys Pro Gly Ile Ala His Arg Asp Leu Ser Ser
                325                 330                 335

Gln Asn Val Leu Ile Arg Glu Asp Gly Ser Cys Ala Ile Gly Asp Leu
            340                 345                 350

Gly Leu Ala Leu Val Leu Pro Gly Leu Thr Gln Pro Pro Ala Trp Thr
        355                 360                 365

Pro Thr Gln Pro Gln Gly Pro Ala Ala Ile Met Glu Ala Gly Thr Gln
    370                 375                 380

Arg Tyr Met Ala Pro Glu Leu Leu Asp Lys Thr Leu Asp Leu Gln Asp
385                 390                 395                 400

Trp Gly Met Ala Leu Arg Arg Ala Asp Ile Tyr Ser Leu Ala Leu Leu
                405                 410                 415

Leu Trp Glu Ile Leu Ser Arg Cys Pro Asp Leu Arg Pro Asp Ser Ser
            420                 425                 430

Pro Pro Pro Phe Gln Leu Ala Tyr Glu Ala Glu Leu Gly Asn Thr Pro
        435                 440                 445

Thr Ser Asp Glu Leu Trp Ala Leu Ala Val Gln Glu Arg Arg Arg Pro
    450                 455                 460

Tyr Ile Pro Ser Thr Trp Arg Cys Phe Ala Thr Asp Pro Asp Gly Leu
465                 470                 475                 480

Arg Glu Leu Leu Glu Asp Cys Trp Asp Ala Asp Pro Glu Ala Arg Leu
                485                 490                 495

Thr Ala Glu Cys Val Gln Gln Arg Leu Ala Ala Leu Ala His Pro Gln
            500                 505                 510
```

-continued

```
Glu Ser His Pro Phe Pro Glu Ser Cys Pro Arg Gly Cys Pro Pro Leu
        515             520             525
Cys Pro Glu Asp Cys Thr Ser Ile Pro Ala Pro Thr Ile Leu Pro Cys
        530             535             540
Arg Pro Gln Arg Ser Ala Cys His Phe Ser Val Gln Gln Gly Pro Cys
545             550             555             560
Ser Arg Asn Pro Gln Pro Ala Cys Thr Leu Ser Pro Val
            565             570
```